US012766140B1

(12) United States Patent
Spina et al.

(10) Patent No.: US 12,766,140 B1
(45) Date of Patent: Oct. 20, 2026

(54) CANCER TREATMENT METHOD COMBINING IMMUNOTHERAPY AND RADIOTHERAPY

(71) Applicant: The Trustees of Columbia University in the City of New York, New York, NY (US)

(72) Inventors: Catherine S. Spina, New York, NY (US); Shruti Bansal, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 496 days.

(21) Appl. No.: 18/317,814

(22) Filed: May 15, 2023

Related U.S. Application Data

(60) Provisional application No. 63/341,961, filed on May 13, 2022.

(51) Int. Cl.

| | |
|---|---|
| ***A61K 31/506*** | (2006.01) |
| ***A61K 31/706*** | (2006.01) |
| ***A61P 35/04*** | (2006.01) |
| ***C07K 16/28*** | (2006.01) |
| *A61K 39/00* | (2006.01) |

(52) U.S. Cl.
CPC .......... *A61K 31/506* (2013.01); *A61K 31/706* (2013.01); *A61P 35/04* (2018.01); *C07K 16/2818* (2013.01); *C07K 16/2827* (2013.01); *A61K 2039/545* (2013.01)

(58) Field of Classification Search
None
See application file for complete search history.

(56) References Cited

U.S. PATENT DOCUMENTS

| | | | |
|---|---|---|---|
| 5,780,597 | A | 7/1998 | Gately et al. |
| 5,811,523 | A | 9/1998 | Trinchieri et al. |
| 6,914,128 | B1 | 7/2005 | Salfeld et al. |

OTHER PUBLICATIONS

Franco, Rafael, et al. "Adenosine receptor antagonists to combat cancer and to boost anti-cancer chemotherapy and immunotherapy." Cells 10.11 (2021): 2831.*

Jennifer Choe, Vanderbilt-Ingram Cancer Center (U.S.). (May 19, 2021 – ). A Study of Concurrent Chemoradiation in Combination With or Without PD1 Inhibitor AB122 Adenosine 2a Receptor / Adenosine 2b Receptor Inhibitor AB928 Therapies in Locally Advanced Head and Neck Cancers (PANTHEoN) [Clinical Trial Registration NCT04892875. Retrieved Oct. 22, 2025, from https://www.clinicaltrials.gov/study/NCT04892875?term=AB928&rank=6.*

Teckie, Sewit, et al. "High-dose hypofractionated radiotherapy is effective and safe for tumors in the head-and-neck." Oral oncology 60 (2016): 74-80.*

Antonioli, Luca, et al. "Switching off CD73: a way to boost the activity of conventional and targeted antineoplastic therapies." Drug discovery today 22.11 (2017): 1686-1696.*

Abuodeh, et al., "Systematic review of case reports on the abscopal effect", Current Problems in Cancer, 40(1):25-37, Jan.-Feb. 2016 (13 pages).

Antonia, et al., "Durvalumab after Chemoradiotherapy in Stage III Non-Small-Cell Lung Cancer", New England Journal of Medicine, 377(20):1919-1929, Nov. 16, 2017 (11 pages).

Hudson, "Recombinant antibody fragments", Current Opinion in Biotechnology, 9(4):395-402, Aug. 1998 (8 pages).

Jhoti, "Fragment-Based Drug Discovery Using Rational Design", Ernst Schering Foundation Symposium Proceedings, 3:169-185, published online Dec 18, 2007 (17 pages).

Al, et al., "Research Status and Outlook of PD-I/PD-LI Inhibitors for Cancer Therapy", Drug Design, Development and Therapy, 14:3625-3649, 2020 (25 pages).

Maynard, et al., "Antibody Engineering", Annual Review of Biomedical Engineering, vol. 2, pp. 339-376, Aug. 2000 (40 pages).

Mensch, et al., "In Vivo, In Vitro and In Silico Methods for Small Molecule Transfer Across the BBB", J. Pharm. Sci., 98(12):4429-4468, Dec 2009 (40 pages).

Postow, et al., "Immunologic Correlates of the Abscopal Effect in a Patient with Melanoma", New England Journal of Medicine, 366(10):925-931, Mar. 8, 2012 (7 pages).

Potyrailo, et al., "Combinatorial and High-Throughput Screening of Materials Libraries: Review of State of the Art", ACS Combinatorial Science, 13(6):579-633, Jun. 6, 2011 (55 pages).

Schnur, "Recent trends in library design: 'Rational design' revisited", Current Opinion in Drug Discovery & Development, 11(3):375-380, May 2008 (6 pages).

Werner, et al., "Joining high-throughput technology with in silico modelling advances genome-wide screening towards targeted discovery", Briefings in Functional Genomics and Proteomics, 5(1):32-36, 2006 (5 pages).

* cited by examiner

*Primary Examiner* — Patrick T Lewis
(74) *Attorney, Agent, or Firm* — Wilmer Cutler Pickering Hale and Dorr LLP

(57) ABSTRACT

The subject matter disclosed herein relates to a method for treating cancer in a subject in need thereof, comprising administering to the subject one or more adenosine signaling modulators in combination with a radiation therapy. In some embodiments, the method further comprises administering to the subject an immune-based therapy.

20 Claims, 46 Drawing Sheets

SABR = stereotactic ablative body radiation

| Histopathology | Study | Age | Gender | Site treated | Radiation used | Technique | Total dose (Gy) | Dose/fraction or duration | Site with abscopal effect | Time for abscopal | Follow-up duration |
|---|---|---|---|---|---|---|---|---|---|---|---|
| RCC | Fairlamb[22] | 73 | F | Pubic bone | EBRT | AP/PA | 40 | 2.6 Gy | Lung | 2 Months | 54 Months |
| RCC | MacManus et al[23] | 53 | M | Renal mass | EBRT | NA | 20 | 2 Gy | Lung and mediastinum | 9 Months | 11 Months |
| RCC | Wersall (2006) | 83 | F | Renal mass | EBRT | SBRT | 32 | 8 Gy | Lymph node and lungs | 2 Years | |
| RCC | Wersall (2006) | 64 | F | Lung lesions | EBRT | SBRT | NA | NA | Lung | NA | 48 Months |
| RCC | Wersall (2006) | 69 | M | Lung lesions | EBRT | SBRT | NA | NA | Lung | NA | 24 Months |
| RCC | Wersall (2006) | 55 | F | Renal mass | EBRT | SBRT | 32 | 8 Gy | Lung | 5 Months | 9 Months |
| RCC | Ishiyama et al[25] | 61 | M | Bone and spine | EBRT | SBRT | 40 | 8 Gy | Lung | 1 Month | 36 Months |
| Melanoma | Kingsley[26] | 28 | M | Inguinal and pelvic lymph nodes | Fast Neutron | NA | 14.4 | 1.2 Gy | Illiac and PA lymph nodes | 2 Months | 17 Months |
| Melanoma | Postow et al[28] | 33 | F | Paraspinal mass | EBRT | IMRT | 28.5 | 9.5 Gy | Hilar lymph node and spleen | 4 Months | 10 months |
| Melanoma | Hiniker et al[29] | 57 | M | Liver lesions | EBRT | SBRT | 54 | 17 Gy | Other liver lesion and subcutaneous nodule in left arm | 4 Months | 12 Months |
| Melanoma | Stamell et al[30] | 67 | M | Skin of scalp | EBRT | 6 MV electron | 24 | 8 Gy | Satellite skin lesions | 8 Months | 84 Months |
| Melanoma | Cabot et al[31] | 63 | M | Brain lesion | EBRT | SRS | NA | NA | Inguinal lymph nodes and bony lesion | 12 Months | 18 Months |
| Melanoma | De la Cruz (2014) | 71 | M | Skin | EBRT | NA | 30 | 3 Gy | Lung and mediastinum | 4 Months | 29 Months |
| Melanoma | Thallinger (2014) | 44 | M | Brain | EBRT | whole brain | 30 | 3 Gy | Lung, liver, renal | 2 Months | 17 Months |

Figure 4

Table Select Ongoing Clinical Trials Testing the Efficacy of Radiation Combined With Immunotherapies in the Setting of Metastatic Cancer to Drive a Systemic Response

| Immunotherapy | Radiotherapy | Trial Phase | NCT Number | Treatment Arms | Endpoints | Enrollment | Eligibility |
|---|---|---|---|---|---|---|---|
| Dendritic cell (DC) vaccine/interferon-alpha (IFNa) | 8-12 Gy x 3 to single nonindex lesion | II | NCT01973322 | DC vaccine only vs DC vaccine + IFNa vs DC vaccine + SBRT vs CD vaccine + IFNa + SBRT | Safety, immune related disease control rate (irDCR), immunologic efficacy (primary), preleukapharesis IFNa effects, OS, immuno-related time to progression (irTTP), irORR, irTTR, TEM-8 expression on DCs | N = 24 | Metastatic melanoma 10/2013 to 08/2020 (estimated) |
| Atezolizumab (anti-PD-L1) | 15 Gy x 5 | II | NCT02992912 SABR-PDL1 | Atezolizumab q3weeks + SBRT to single metastasis | PFS | N = 187 | Metastatic CRC, NSCLC, RCC, and sarcoma, minimum of 2 metastatic lesions 10/2016 to 10/2020 (estimated) |
| Nivolumab (anti-PD-1), pembrolizumab (anti-PD-1), atezolizumab (anti-PD-L1) | 10 Gy x 3 to 1 lesion | II | NCT03115801 | Nivolumab / pembrolizumab / atezolizumab vs nivo / pembro / atezo / SBRT | Best ORR to single metastatic site (primary), PFS, toxicity, OS | N = 112 | Metastatic RCC and urothelial carcinoma, minimum of 2 metastatic lesions 11/2016 to 12/2022 (estimated) |
| Ipilimumab (anti-CTLA-4) / Nivolumab (anti-PD-1) | 6 Gy x 3 | II | NCT03071406 | Ipilimumab / nivolumab vs ipi / nivo / SBRT | ORR (primary), PFS, OS | N = 50 | Metastatic Merkel cell carcinoma, minimum of 2 metastatic lesions 03/2017 to 07/2023 (estimated) |
| Tremelimumab (anti-CTLA-4) / Durvalumab (anti-PD-L1) | Low-dose: 0.5 Gy BID x 2 days q4weeks x 4 cycles; High-dose: 8 Gy x 3 | II | NCT02888743 | Durvalumab / tremelimumab vs durva / treme / high dose RT vs durva / treme / low dose RT | ORR (primary), PFS, OS, irORR, LC, PD-L1 expression, T-cell infiltration, AEs | N = 180 | Metastatic CRC and NSCLC 08/2017 to 12/2020 (estimated) |
| Durvalumab (anti-PD-L1) | 8 Gy x 5 to 1 lesion, 3 Gy x 5 to a second lesion | II | NCT02885727 (Panc-Durval+RT) | Durvalumab / RT | PFS | N = 55 | Metastatic pancreatic cancer, minimum of 2 metastatic lesions |
| Durvalumab (anti-PD-L1) | Radioactive iodine (RAI) | Pilot | NCT03215095 | Durvalumab / 100mCi (+/- 10 mCi) | DLTs (primary), best ORR | N = 11 | Recurrent / metastatic thyroid cancers 07/2017 to 07/2021 |
| Oncolytic virus (AVD/HSV-tk), valcyclovir, pembrolizumab (anti-PD-1) | 6 Gy x 5 to a single lesion | II | NCT03004183 | ADV/HSV-tk / valcyclovir / SBRT followed by pembrolizumab | ORR (primary), duration of response, OS, PFS, AEs, anti-tumor activity, clinical benefit | N = 57 | Metastatic triple negative breast cancer or NSCLC, minimum of 2 metastatic lesions |

Figure 6

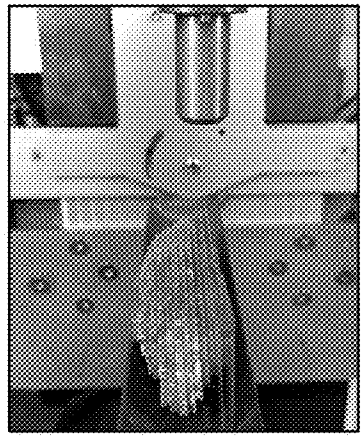
| | Measured Dose (cGy) | | Max Deviation |
|---|---|---|---|
| 80cGy coronal | 80.8 | nd | 1.0% |
| 80cGy sagittal | 80.9 | 81 | 1.25% |
| 800cGy coronal | 782.4 | 815.3 | 2.2% |
| 800cGy sagittal | 813.9 | 811.3 | 1.74% |
Figure 12

Myeloid Signature: Leading Edge Genes
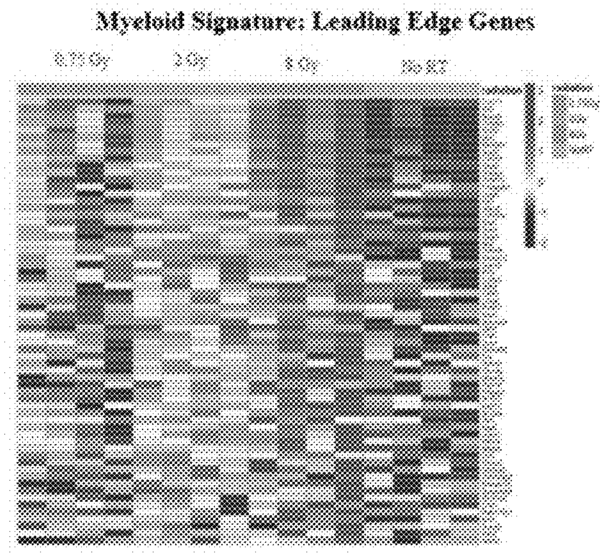
| Index | Name | P-value | Adjusted p-value | Odds Ratio | Combined score |
|---|---|---|---|---|---|
| 1 | Type II interferon signaling (IFNG) WP1253 | 3.397e-11 | 5.979e-9 | 8.53 | 205.50 |
| 2 | p53 signaling WP2902 | 2.187e-7 | 0.00001925 | 4.61 | 70.77 |
| 3 | TYROBP Causal Network WP3625 | 0.00003390 | 0.001989 | 4.00 | 41.15 |
| 4 | Nucleotide GPCRs WP207 | 0.002526 | 0.04042 | 6.44 | 38.53 |
| 5 | Apoptosis WP1254 | 0.00006422 | 0.002260 | 3.34 | 32.24 |
| 6 | IL-5 Signaling Pathway WP151 | 0.0001984 | 0.004989 | 3.36 | 28.65 |
| 7 | IL-6 signaling Pathway WP387 | 0.0001679 | 0.004926 | 2.93 | 25.45 |
| 8 | Chemokine signaling pathway WP2292 | 0.00004876 | 0.002146 | 2.44 | 24.23 |
| 9 | IL-2 Signaling Pathway WP450 | 0.0005009 | 0.01102 | 3.05 | 23.19 |
| 10 | Notch Signaling Pathway WP29 | 0.002261 | 0.03979 | 3.36 | 20.47 |
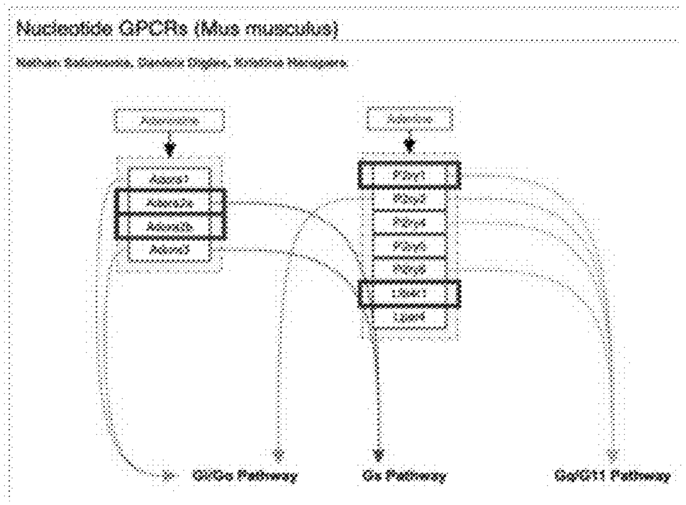
Figure 18

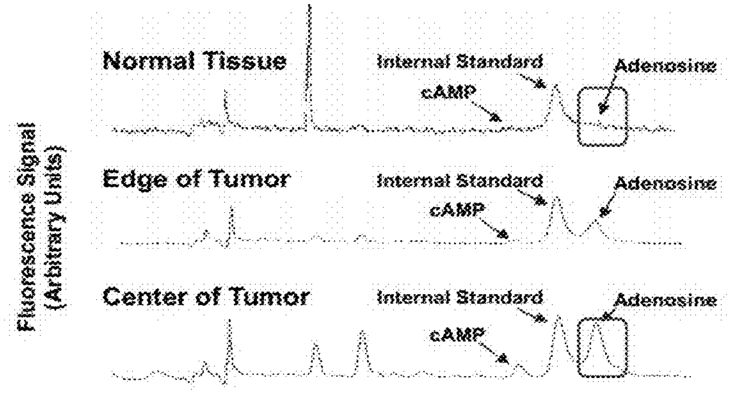
At baseline, extracellular adenosine in tumor tissue is significantly more abundant that normal tissue.
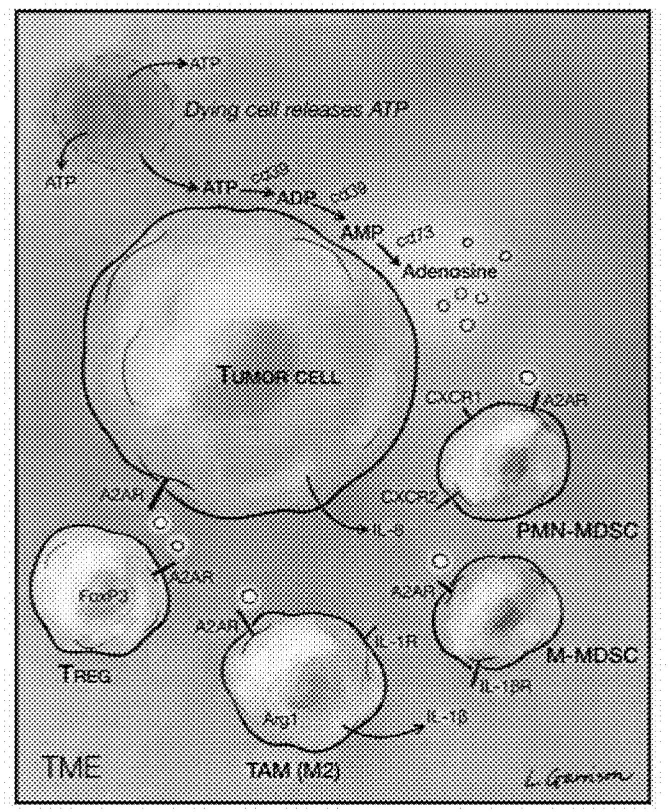
Figure 21

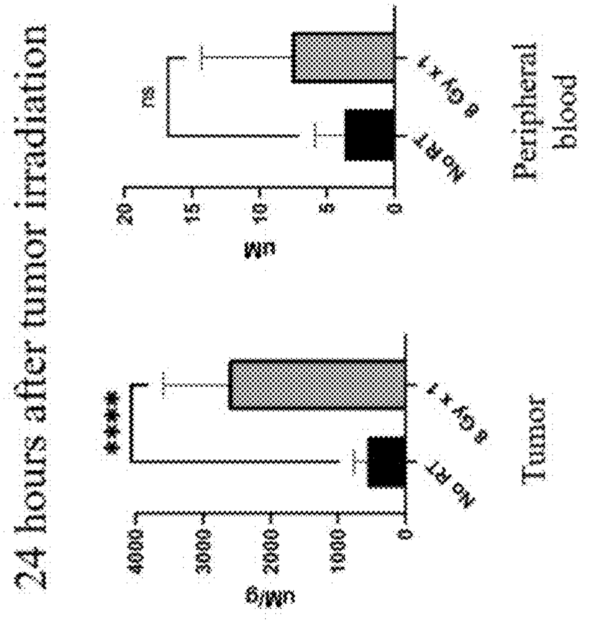
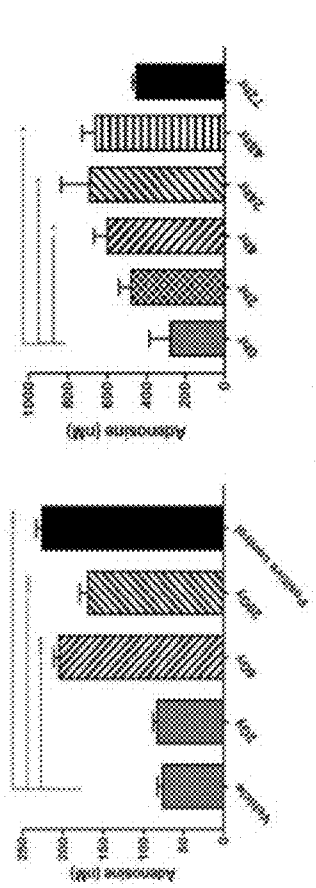
Radiation further increases extracellular adenosine in mouse MC38 tumors 4-48 hours post-RT (5 Gy)
Figure 22

| | IFN-β | TGF-b |
|---|---|---|
| DMSO | 44 (100%) | nd |
| 0.1mM NECA | 19 (44%) | nd |
| 1mM NECA | 80 (183%) | nd |
| 10mM NECA | 772 (1771%) | 60 |
| 10mM NECA - no stim | 1993 (4574%) | 82 |

(c)

CANCER TREATMENT METHOD COMBINING IMMUNOTHERAPY AND RADIOTHERAPY

CROSS REFERENCE TO RELATED APPLICATION

The application claims the benefit of and priority to U.S. Provisional Application No. 63/341,961, filed on May 13, 2022, the content of which is hereby incorporated by reference its entirety.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND

Radiotherapy or radiation therapy (RT) is an integral component of multidisciplinary cancer care. It is used in more than 50% of all cancer patients as curative or palliative treatment. RT induces DNA damage, which can lead to tumor cell death through senescence, apoptosis, necrosis and mitotic catastrophe. Cancer is no longer treated in a binary fashion, either localized cancer or metastatic cancer. There are limited options for treating an intermediate disease state, meaning patients with low volume or oligometastatic disease.

SUMMARY

In certain aspects, the present application provides a method for treating cancer in a subject in need thereof, comprising administering to the subject one or more adenosine signaling modulators in combination with a radiation therapy.

In some embodiments, the method further comprises administering to the subject an immune-based therapy.

In some embodiments, the immune-based therapy comprises administering to the subject a therapeutic agent that activates the immune system of the subject.

In some embodiments, the immune-base therapy comprises administering to the subject a therapeutic agent that suppresses the immune system of the subject.

In some embodiments, the immune-base therapy comprises administering to the subject a therapeutic agent that regulates programmed cell death protein 1 (PD-1), programmed Cell Death Ligand 1 (PD-L1), or combination thereof.

In some embodiments, the therapeutic agent is selected from one or more of pembrolizumab, nivolumab, cemiplimab, dostarlimab, atezolizumab, ipilimumab, avelumab, zimberelimab, and durvalumab.

In some embodiments, the method further comprises administering to the subject an adenosine signaling modulator.

In some embodiments, the adenosine signaling modulator is an A2AR and A2BR antagonist or a CD73 antagonist.

In some embodiments, the adenosine signaling modulator is etrumadenant.

In some embodiments, the adenosine signaling modulator is quemliclustat.

In some embodiments, the cancer comprises a solid tumor.

In some embodiments, the cancer is one or more of breast cancer, pancreatic cancer, prostate cancer, melanoma, basal cell cancer, colorectal cancer, bladder cancer, kidney cancer, thyroid cancer, uterine cancer, or lung cancer.

In some embodiments, the cancer is metastatic.

In some embodiments, the cancer is oligometastatic.

In some embodiments, the subject is a human.

In some embodiments, the radiation therapy is administered for 1 day, 2 days, 3 days, 4 days, 5 days, 6 days, or 7 days.

In some embodiments, the radiation therapy is administered at a dose of about 8 gray.

BRIEF DESCRIPTION OF THE DRAWINGS

The patent or application file contains at least one drawing in color. Many of the figures presented herein are black and white representations of images originally created in color.

FIG. 4 shows radiotherapy alone is unlikely to induce abscopal responses.

FIG. 6 shows selected ongoing clinical trials testing the efficacy of radiation therapy combined with immunotherapies in the setting of metastatic cancer to drive a systemic response.

FIG. 12 shows radiation dose verification.

FIG. 18 shows irradiation and bulk transcriptomic changes.

FIG. 21 shows adenosine signaling pathway and the abundance of adenosine in tumor cells.

FIG. 22 shows adenosine concentration after 48 hrs (left) and 24 hrs (right) radiotherapy.

FIG. 33C provides a graph showing that radiation drives a dose-dependent increase in expression of adenosine signaling genes in tumor infiltrating CD45+ immune compartment in murine tumors.

FIG. 37A shows one example of a treatment protocol over time and FIG. 37B is a graph showing changes in tumor volume over time for various treatments.

FIG. 38A to FIG. 38F are graphs showing changes in tumor volume over time for various treatments.

DETAILED DESCRIPTION

The singular forms “a”, “an” and “the” include plural reference unless the context clearly dictates otherwise. The use of the word “a” or “an” when used in conjunction with the term “comprising” in the claims and/or the specification may mean “one,” but it is also consistent with the meaning of “one or more,” “at least one,” and “one or more than one.”

As used herein the term “about” is used herein to mean approximately, roughly, around, or in the region of. When the term “about” is used in conjunction with a numerical range, it modifies that range by extending the boundaries above and below the numerical values set forth. In general, the term “about” is used herein to modify a numerical value above and below the stated value by a variance of 20 percent up or down (higher or lower).

An “effective amount”, “sufficient amount” or “therapeutically effective amount” as used herein is an amount of a compound that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the compound that avoids or substantially attenuates undesirable side effects.

Methods of Treatment

The indications for radiotherapy have been expanding. The conventional indications include curative intent (e.g., definitive radiotherapy for prostate cancer, chemoradiation for lung cancer) and palliative intent (e.g., pain from metastatic disease, prevention or treatment of pathologic fracture). The emerging goals now include 1) ablative treatment for oligometastatic disease (phase II data, phase III ongoing) to improve PFS, OS; and 2) ablative treatment for oligoprogressive disease to keep patients off of toxicity therapy (improve QOL, delay hormonal therapy for metastatic prostate cancer, toxic chemotherapy).

Figures 1A, 1B:
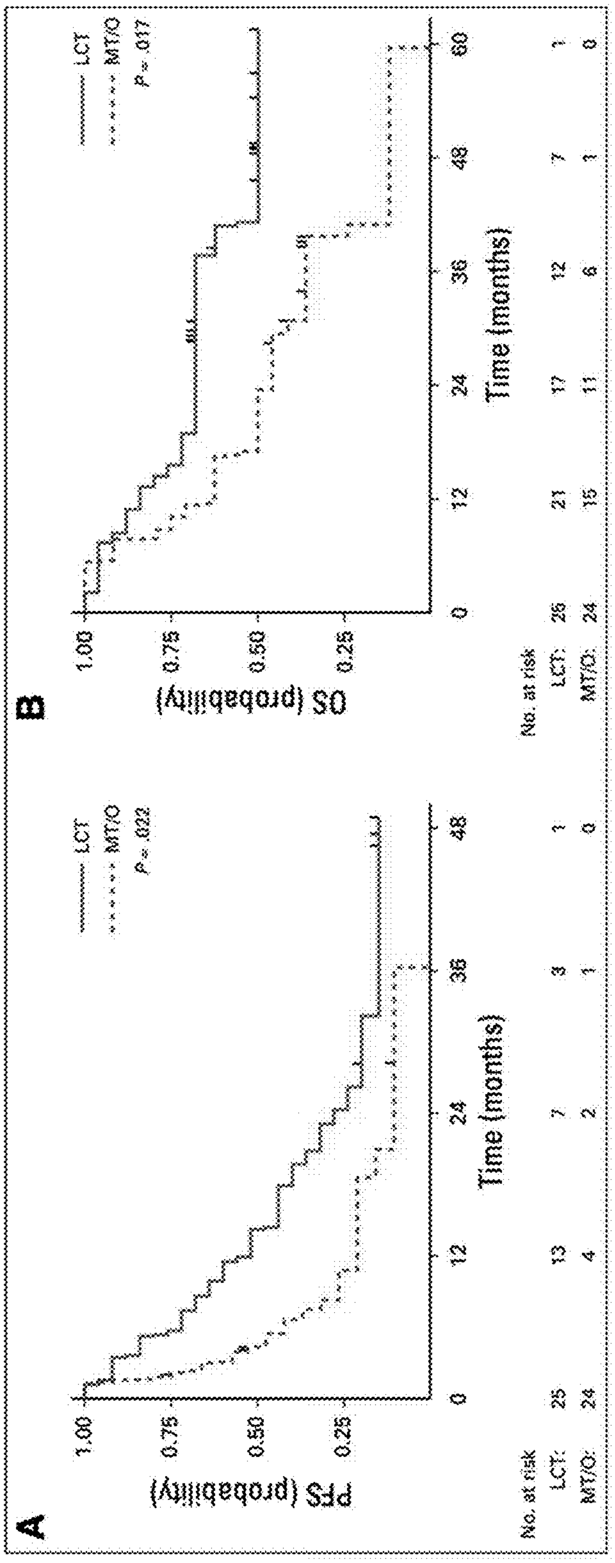
FIGS. 1A-B show phase II non-small cell lung cancer (NSCLC) in an oligometastatic patient (≤3 mets) with local consolidative therapy (LCT) and maintenance therapy or observation (MT/O).
Figures 2A, 2B:
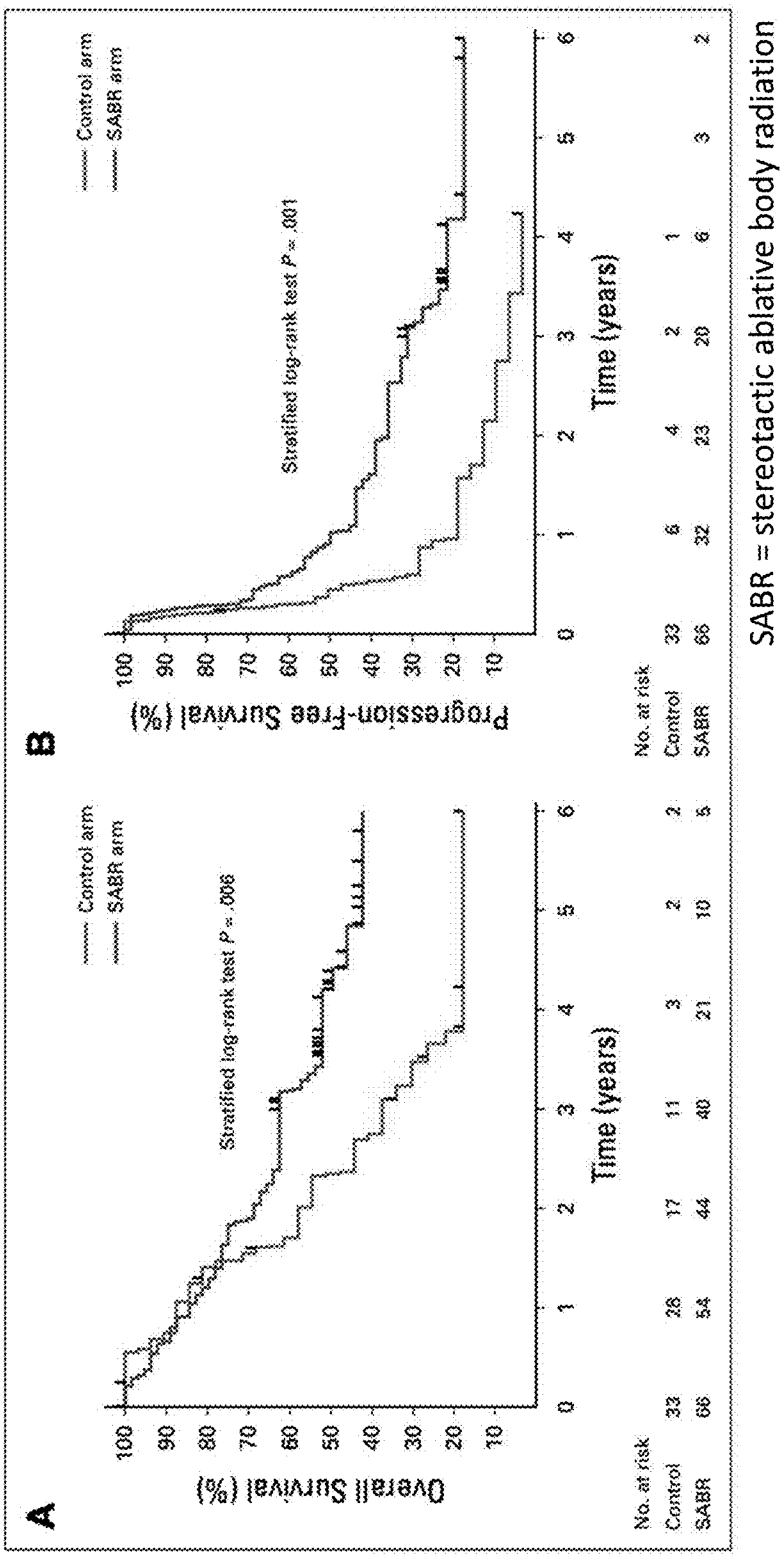
FIGS. 2A-B show the survival rates by control arm and stereotactic ablative body radiation arm.
Figures 3A, 3B, 3C, 3D, 3E, 3F:
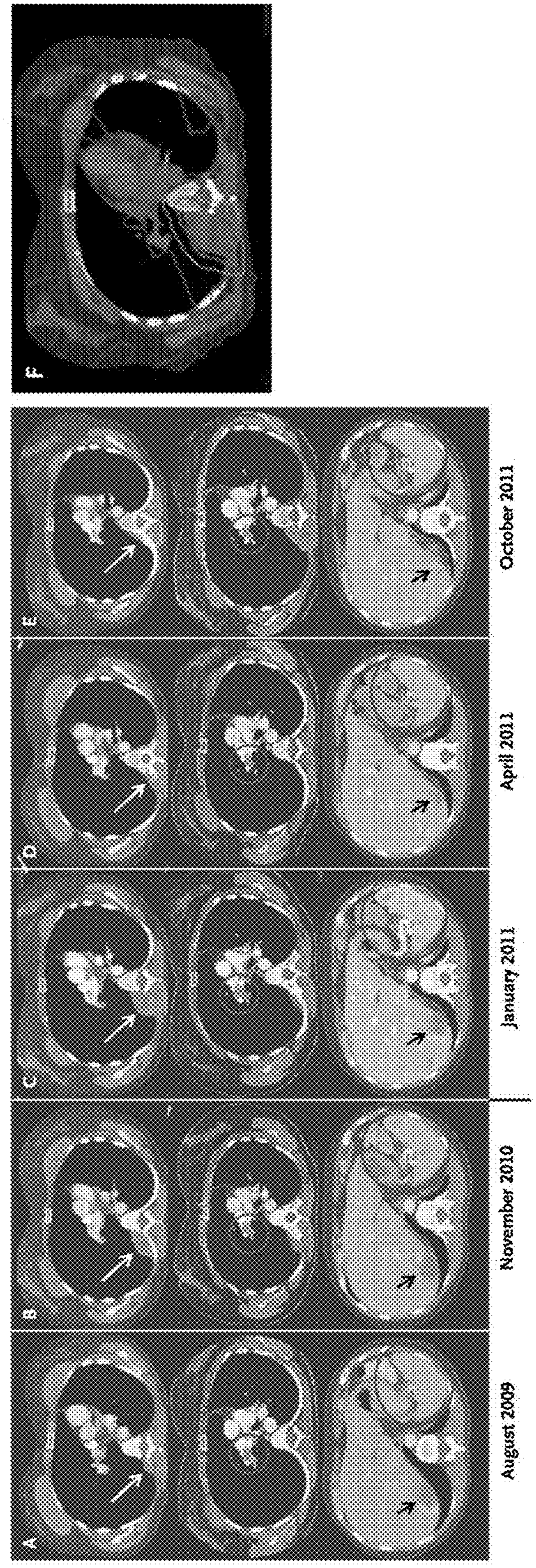
FIGS. 3A-F shows that radiotherapy can illicit systemic responses in one patient with metastatic melanoma.

In certain cases, radiotherapy can illicit systemic responses. For example, a 38-year-old woman with metastatic melanoma was enrolled on a clinical trial testing ipilimumab (anti-CTLA-4) in September 2009. In November 2010, the progression of pleural based disease was noticed and then she was offered with palliative radiotherapy 2850 cGy (low dose). In January 2011, no response to RT was seen. Thus, one month later, the patient was given one additional dose of ipilimumab. By April 2011, significant regression of all sites of disease was seen with persistent stability 10 months later. However, abscopal responses are exceptionally rare. Only a total of 46 cases reports of abscopal responses were found from 1998 to 2014. In the meanwhile, FDA-approved several immunotherapies by the end of 2014, including ipilimumab (melanoma, 03/2011), pembrolizumab (melanoma, 09/2014), and nivolumab (melanoma, 12/2014). It seems radiotherapy might be able to induce a more meaningful clinical response to immunotherapy alone. However, radiotherapy alone is unlikely to induce abscopal responses (see FIG. 3).

Figure 5:
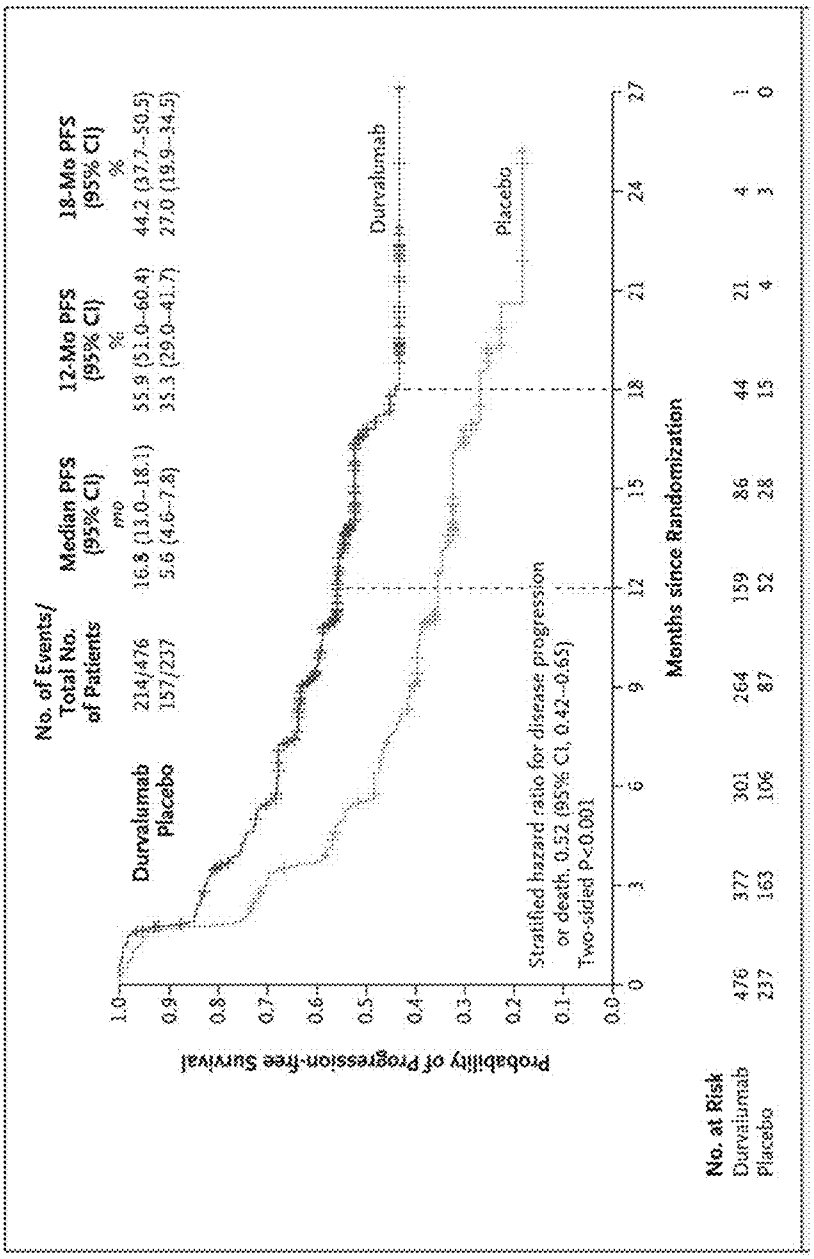
FIG. 5 shows PD-L1 (1-42 days) treatment after definitive chemoradiation for patients with unresectable, stage III NSCLC (n=300). The chart shows a comparison between durvalumab+chemoradiation treatment and placebo+chemoradiation treatment.
Figure 7:
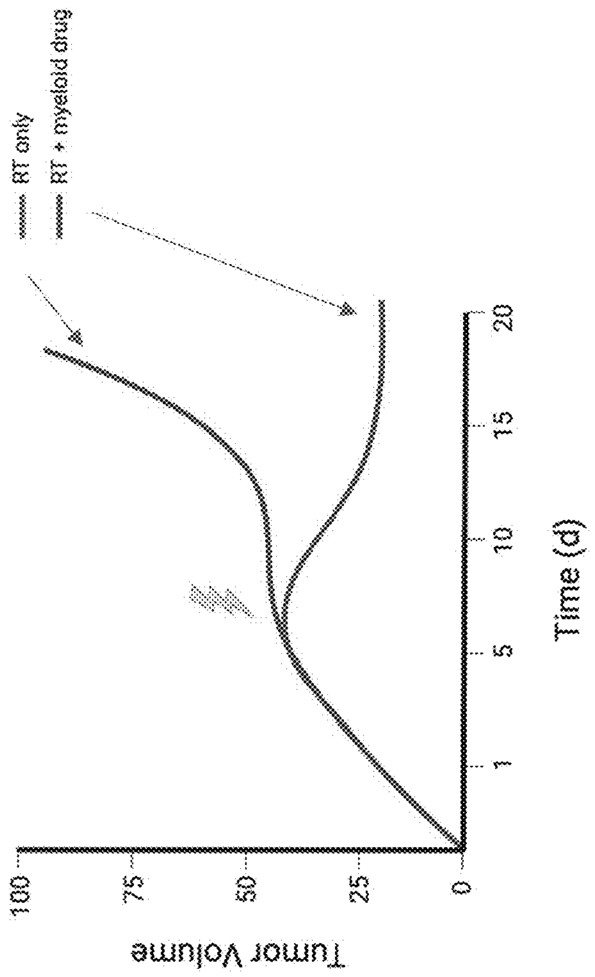
FIG. 7 shows the rational design and development of systemic immune-based therapies for combination with radiation delivered with a curative, palliative, and consolidative intent.

In another example, durvalumab (an FDA-approved immunotherapy drug) showed improved survival rates when combined with chemoradiation (see FIG. 5). However, there is currently no immunotherapy that is approved by the FDA for combination with radiotherapy.

Figure 8:
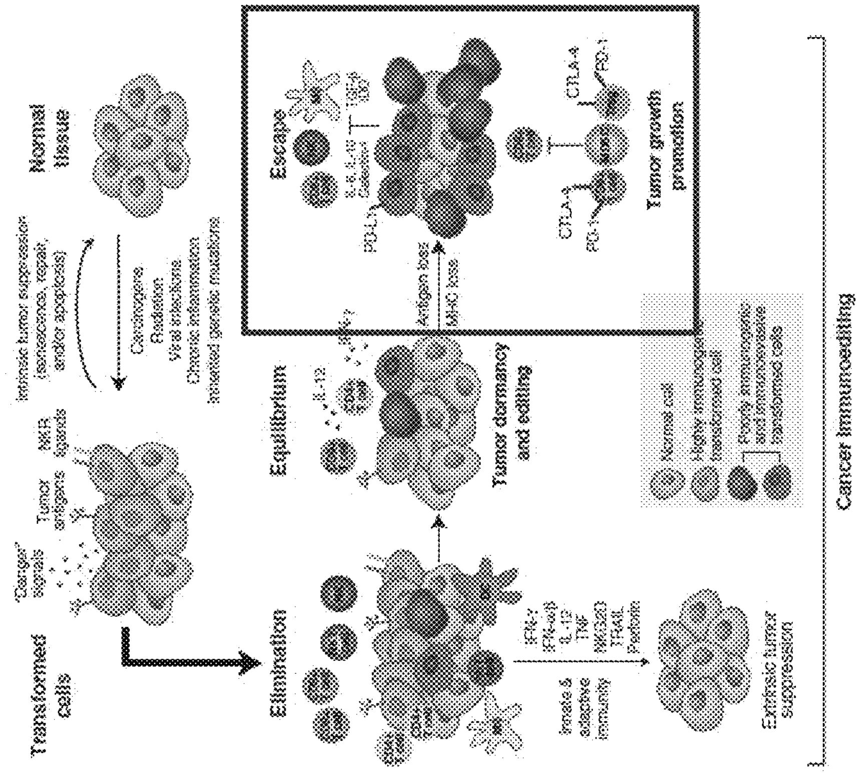
FIG. 8 shows immunoediting and selection of cancer cells.
Figure 9:
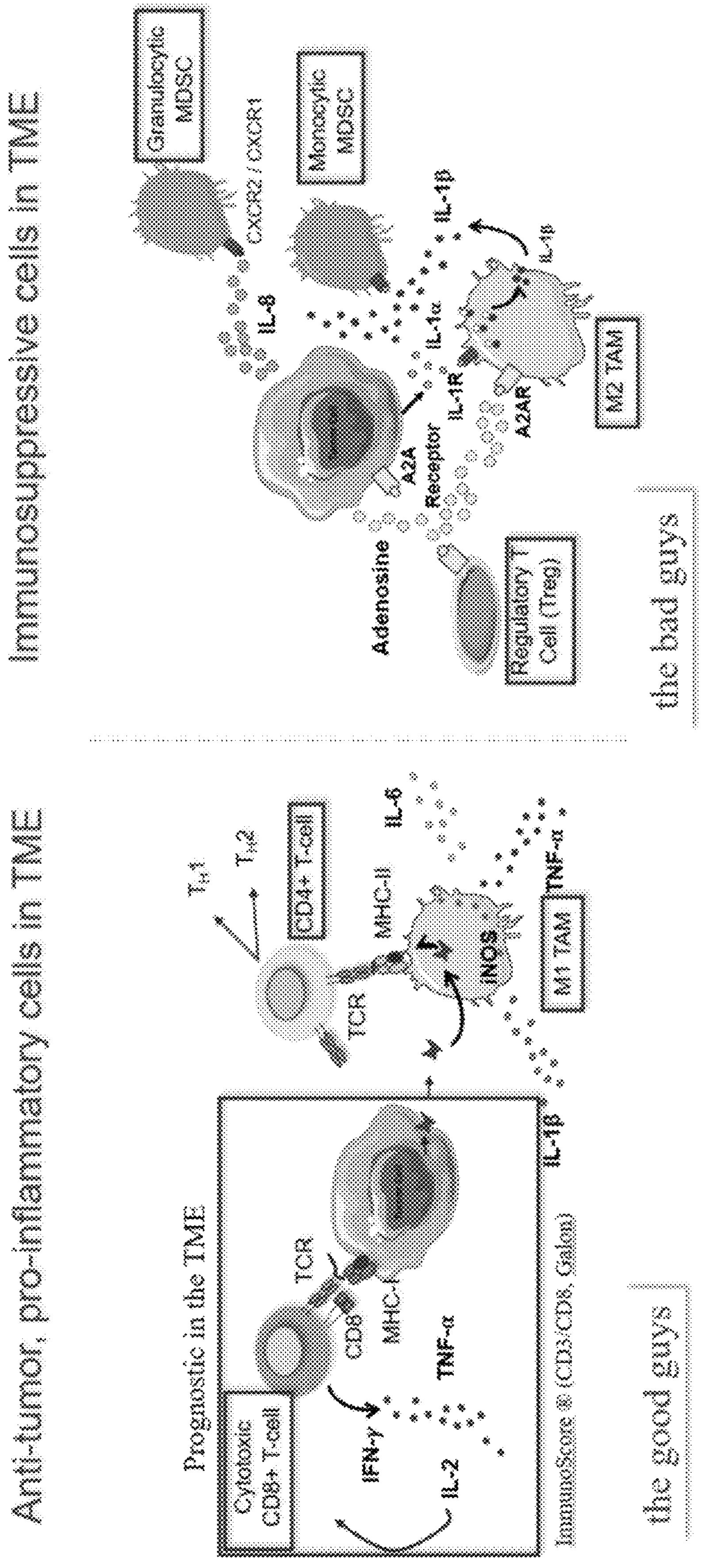
FIG. 9 shows anti-tumor, pro-inflammatory cells (left) and immunosuppressive cells (right) in the tumor immune microenvironment (TME).
Figure 10:
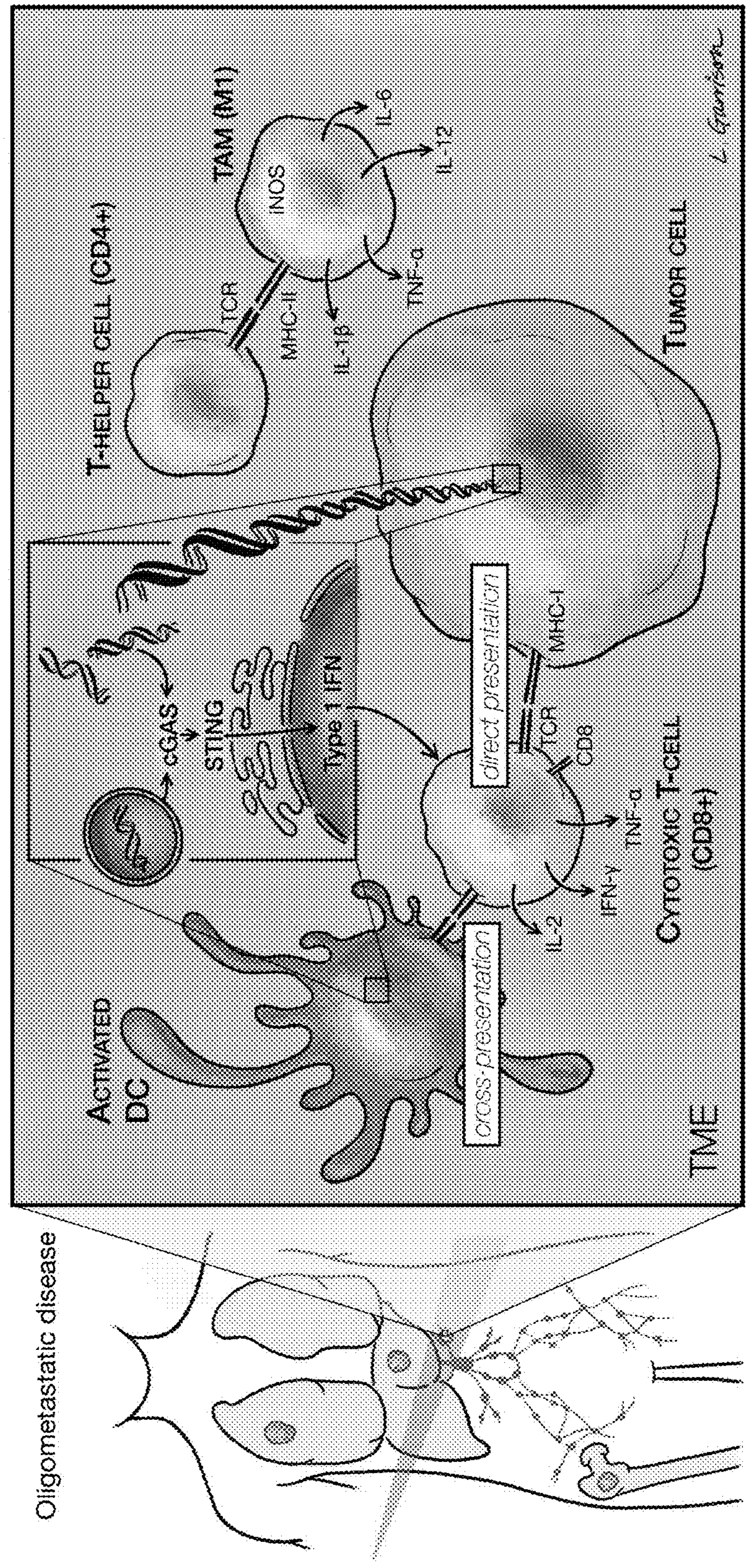
FIG. 10 shows the tumor immune microenvironment (TME) in a patient with oligometastatic disease.

In some embodiments, the combined therapy in the instant application is aimed to a) reinvigorate response, and/or (b) augment a systemic anti-tumor immune response. There is an equilibrium for the immunoediting and selection for cancer cells (selection for genetically unstable cells) (see FIG. 8). When the unstable cells are selected, they are no longer recognized by adaptive immune system (e.g., antigen loss). They become insensitive to effector mechanisms (e.g., PD1/PDL1). Thus, they induce an immunosuppressive state in the TME.

In certain aspects, the present application provides a method for treating cancer in a subject in need thereof, comprising administering to the subject one or more adenosine signaling modulators in combination with a radiation therapy. In some embodiments, the method further comprises administering to the subject an immune-based therapy.

In certain aspects, the present application provides a method for reducing or inhibiting proliferation of tumor cells or inhibiting tumor metastasis in a subject in need thereof, comprising administering to the subject one or more adenosine signaling modulators in combination with a radiation therapy. In some embodiments, the method further comprises administering to the subject an immune-based therapy.

In certain aspects, the present application provides a method for treating tumor reoccurrence in a subject in need thereof, comprising administering to the subject one or more adenosine signaling modulators in combination with a radiation therapy. In some embodiments, the method further comprises administering to the subject an immune-based therapy.

In some embodiments, radiation induces immunogenic cell death including the release of intracellular ATP from dying cells. ATP is quickly metabolized by ectonucleotidases (CD39 & CD73) to immunosuppressive adenosine. At baseline, adenosine concentration is significantly higher in tumor, compared to normal surrounding tissue. Modulation of adenosine signaling can sensitize the tumor to improve the efficacy of immune-based therapies, such as immune checkpoint inhibitors. Thus, adding an adenosine signaling modulator can improve the efficacy of the therapy.

In certain aspects, the present application provides a method for treating cancer in a subject in need thereof, comprising administering to the subject an A2AR and A2BR antagonist, a CD73 antagonist, or a combination thereof, in combination with a radiation therapy. In some embodiments, the method comprises administering an A2AR and A2BR antagonist and a CD73 antagonist in combination with a radiation therapy.

In certain aspects, the present application provides a method for reducing or inhibiting proliferation of tumor cells or inhibiting tumor metastasis in a subject in need thereof, comprising administering to the subject an A2AR and A2BR antagonist, a CD73 antagonist, or a combination thereof, in combination with a radiation therapy. In some embodiments, the method comprises administering an A2AR and A2BR antagonist and a CD73 antagonist in combination with a radiation therapy.

In certain aspects, the present application provides a method for treating tumor reoccurrence in a subject in need thereof, comprising administering to the subject an A2AR and A2BR antagonist, a CD73 antagonist, or a combination thereof, in combination with a radiation therapy. In some embodiments, the method comprises administering an A2AR and A2BR antagonist and a CD73 antagonist in combination with a radiation therapy.

In some embodiments, the A2AR and A2BR antagonist is compound AB928 also known as etrumadenant. In some embodiments, the CD73 antagonist is compound AB680 also known as quemliclustat. In some embodiments, the method further comprises administering to the subject an immune checkpoint inhibitor. In some embodiments, the immune checkpoint inhibitor is an anti-PD1 monoclonal antibody or an anti-PD-L1 monoclonal antibody. In some embodiments, the immune checkpoint inhibitor is anti-PD1 monoclonal antibody zimberelimab.

In some embodiments, the method comprises administering the A2AR and A2BR antagonist, CD73 antagonist, or a combination thereof, to the subject before radiation therapy. In some embodiments, the A2AR and A2BR antagonist, CD73 antagonist, or a combination thereof is administered for at least 1 day, 2 days, 3 days, 4 days, 5 days, 6 days, 7 days, 8 days, 9 days, or 10 days before radiation therapy. In some embodiments, the A2AR and A2BR antagonist, CD73 antagonist, or a combination thereof is administered for at least 5 days before radiation therapy. In some embodiments, the A2AR and A2BR antagonist, CD73 antagonist, or a combination thereof continues to be administered during the radiation therapy treatment. In some embodiments, the A2AR and A2BR antagonist, CD73 antagonist, or a combination thereof continues to be administered after the radiation therapy treatment (e.g., overlapping in administration with the immune checkpoint inhibitor). In some embodiments, the A2AR and A2BR antagonist, CD73 antagonist, or a combination thereof continues to be administered after treatment with the immune checkpoint inhibitor is completed.

In some embodiments, the radiation therapy is administered for 1 day, 2 days, 3 days, 4 days, 5 days, 6 days, or 7 days. In some embodiments, the radiation therapy is administered on consecutive days. In some embodiments, the radiation therapy is administered for 3 consecutive days.

In some embodiments, the radiation therapy is administered at a dose of about 8 gray. In some embodiments, the radiation therapy is administered at a dose of 8 gray.

Some non-limiting examples of radiation therapy include: external beam radiation therapy, sealed source radiation therapy, unsealed source radiation therapy, particle therapy, and radioisotope therapy.

In some embodiments, the immune checkpoint inhibitor is administered after the radiation therapy. In some embodiments, the first dose of the immune checkpoint inhibitor is administered on the last day of the radiation therapy. In some embodiments, the first dose of the immune checkpoint inhibitor is administered on the day after the radiation therapy is completed. In some embodiments, the immune checkpoint inhibitor is administered at least 5 times, 6 times, 7 times, 8 times, 9 times, or 10 times. In some embodiments, the immune checkpoint inhibitor is administered at least 5 times. In some embodiments, the immune checkpoint inhibitor is administered every other day.

In some embodiments, the immune-based therapy (or immunotherapy) comprises administering to the subject a therapeutic agent that activates the immune system of the subject. In some embodiments, the immune-base therapy comprises administering to the subject a therapeutic agent that suppresses the immune system of the subject. In some embodiments, the immune-base therapy comprises an immune checkpoint inhibitor. In some embodiments, the immune-base therapy comprises administering to the subject a therapeutic agent that regulates programmed cell death protein 1 (PD-1), programmed Cell Death Ligand 1 (PD-L1) or a combination thereof. In some embodiments, the immune-base therapy, such as an immune checkpoint inhibitor is an anti-PD1 monoclonal antibody. See Ai L, Chen J, Yan H, He Q, Luo P, Xu Z, Yang X. Research Status and Outlook of PD-1/PD-L1 Inhibitors for Cancer Therapy. Drug Des Devel Ther. 2020 Sep. 8; 14:3625-3649, the content of which, including the description of FDA approve immune checkpoint inhibitors, is hereby incorporated by reference in its entirety. In some embodiments, the therapeutic agent is selected from the group consisting of pembrolizumab, nivolumab, cemiplimab, dostarlimab, atezolizumab, ipilimumab, avelumab, durvalumab, zimberelimab and combinations thereof.

In some embodiments, the cancer comprises a solid tumor. In some embodiments, the cancer is breast cancer. In some embodiments, the cancer is pancreatic cancer. In some embodiments, the cancer is prostate cancer. In some embodiments, the cancer is melanoma. In some embodiments, the cancer is basal cell cancer. In some embodiments, the cancer is colorectal cancer. In some embodiments, the cancer is bladder cancer. In some embodiments, the cancer is kidney cancer. In some embodiments, the cancer is thyroid cancer. In some embodiments, the cancer is uterine cancer. In some embodiments, the cancer is lung cancer.

In some embodiments, the subject is an animal. In some embodiments, the subject is a mammal. In some embodiments, the subject is a human. Tumor growth can be measured in a variety of ways, known to one of skill in the art. For example, tumor growth can be measured by measuring the tumor volume over time. Tumor volume can be measured in a variety of ways, known to one of skill in the art including, but not limited to, positron emission tomography and computed tomography (PET-CT), single-photon emission computed tomography (SPECT-CT), magnetic resonance spectroscopy (MR), X-ray computed tomography (CT), and molecular imaging.

Figure 11:
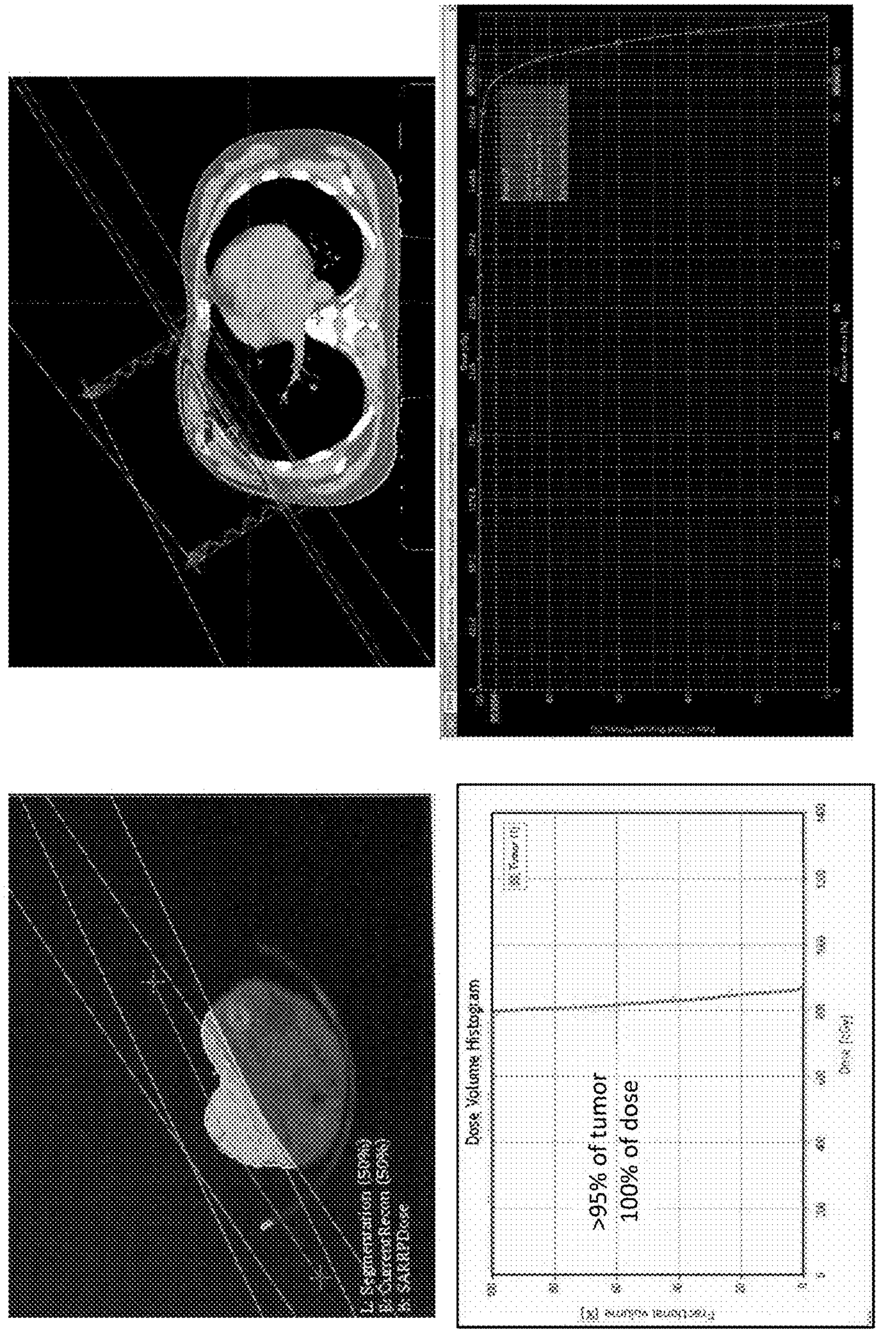
FIG. 11 shows radiation treatment planning by Small Animal Radiation Research Platform (SARRP).

In some embodiments, RT is delivered using the Small Animal Radiation Research Platform (SARRP, Xstrahl, 220 kV) that enables image-guidance and rigorous dosimetric analyses as shown in FIG. 11. SARRP delivers targeted radiation to pre-clinical animal models with an accuracy equivalent to clinical radiotherapy. SARRP enables on-board high resolution cone beam-CT imaging. SARRP is capable of generating micro beams (down to 0.5 mm) of radiation to an accuracy of 200 μm. The SARRP allows the user to image the animal, contour the tumor or organ at risk (OAR), and evaluate the radiation dose. Dose verification QA studies of SARRP were conducted using radiochromic film to confirm the actual dose delivered to the tumor as shown in FIG. 12. These studies confirmed an accuracy within 1-2% of the prescribed dose.

Figure 13:
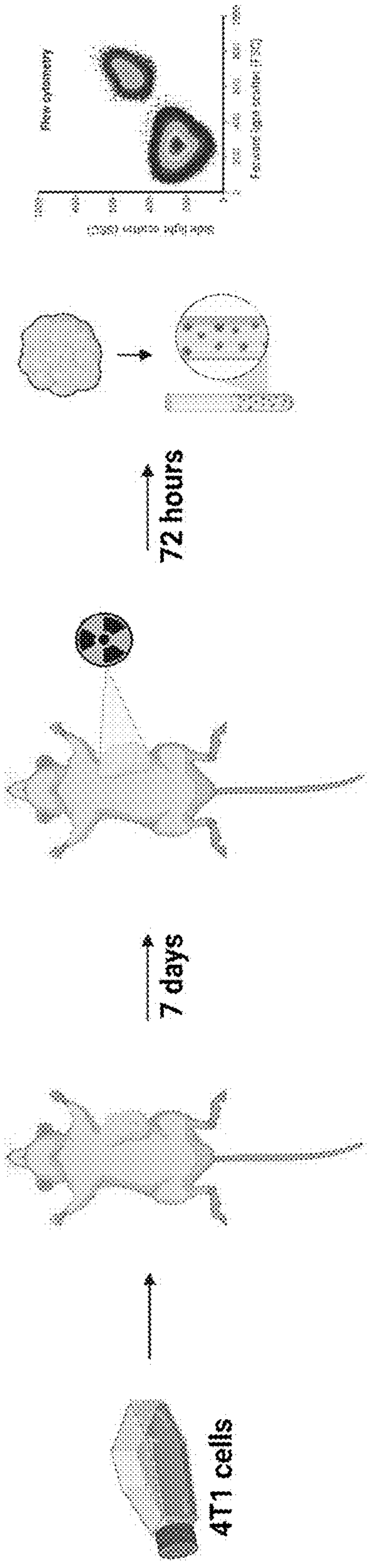
FIG. 13 shows the combined therapy of radiation with immunotherapy in an orthotopic 4T1 breast cancer model.
Figure 14:
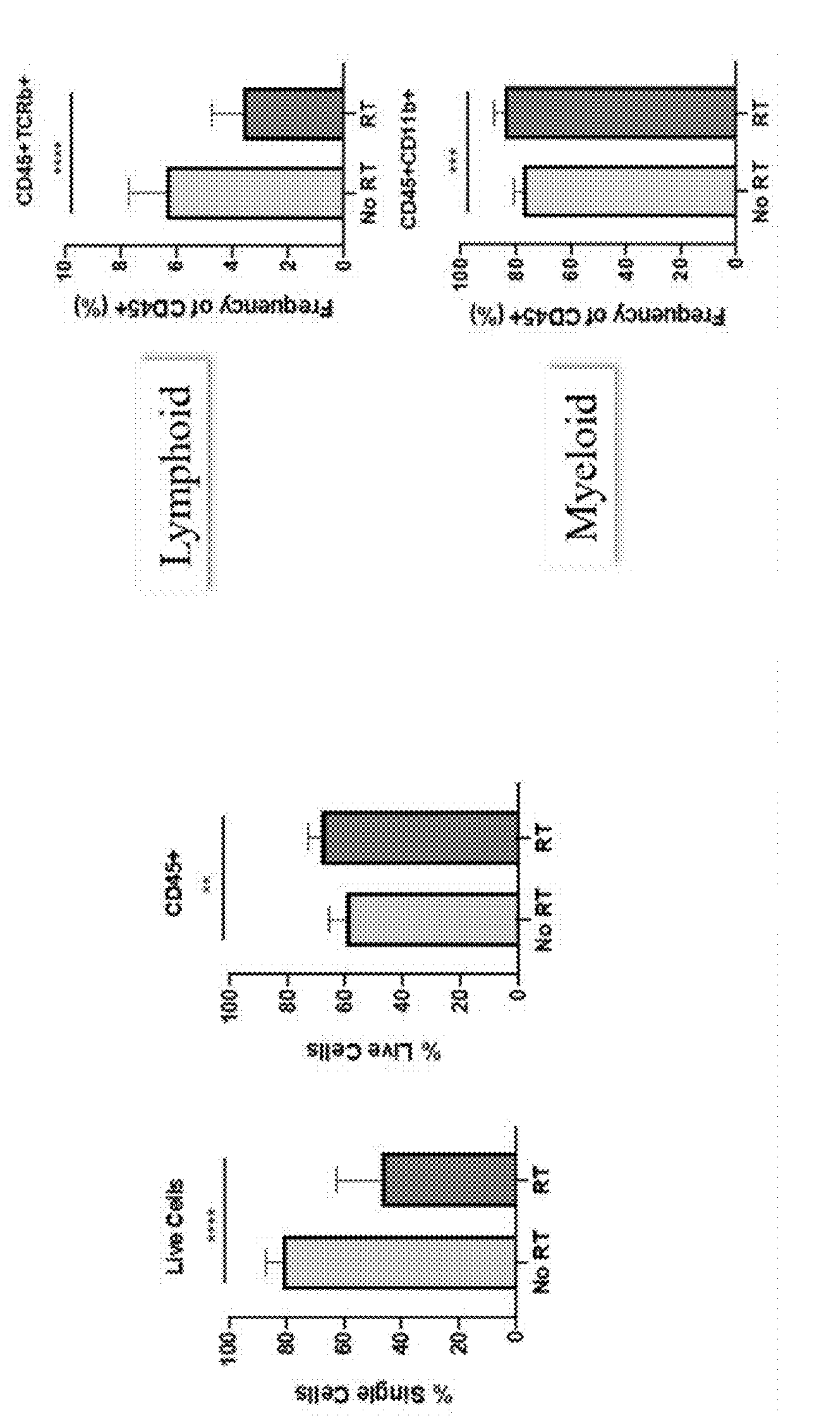
FIG. 14 shows the immune compartment 72-hours after tumor irradiation.
Figure 15:
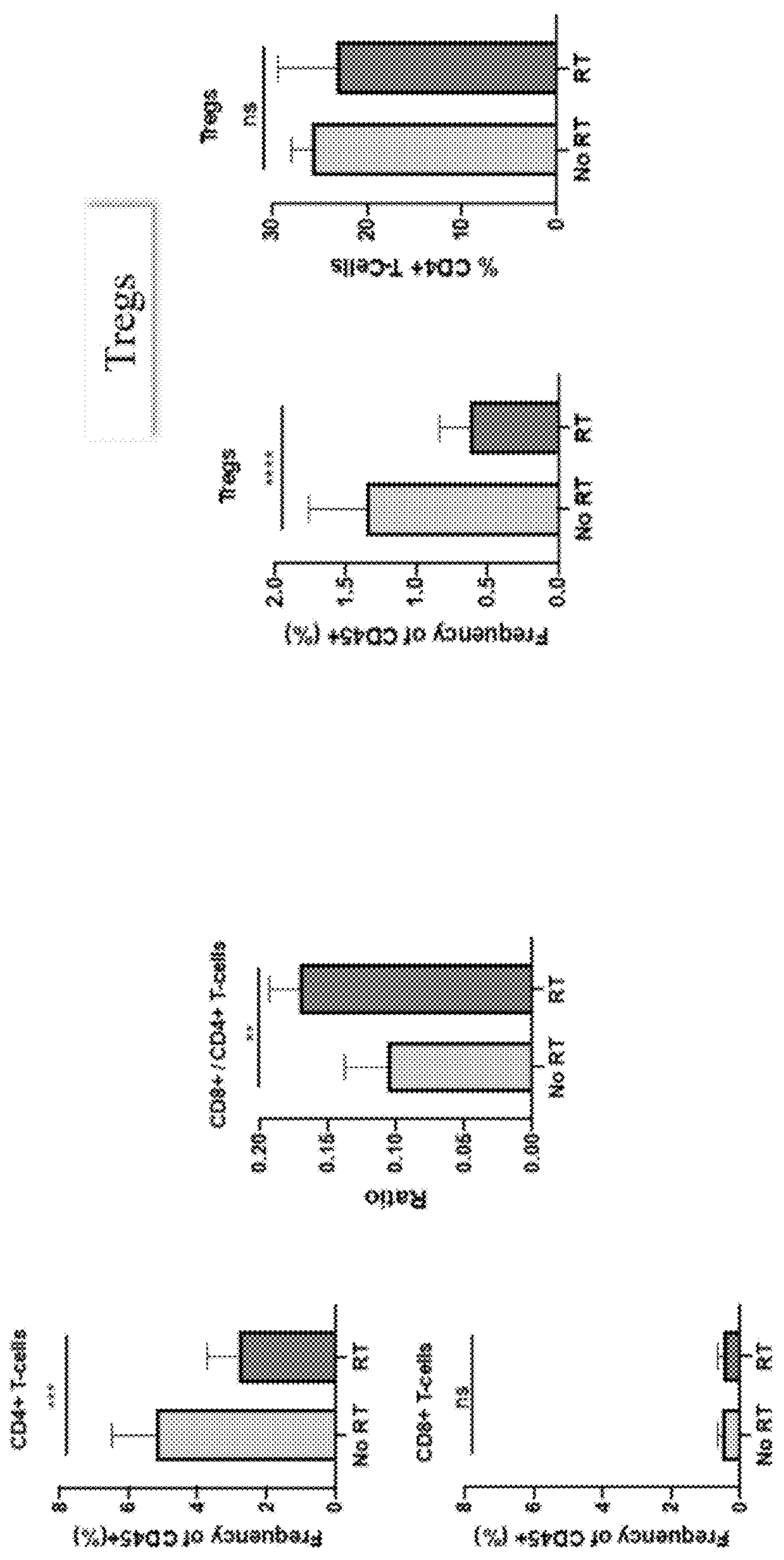
FIG. 15 shows lymphoid compartment 72-hours after tumor irradiation
Figure 16:
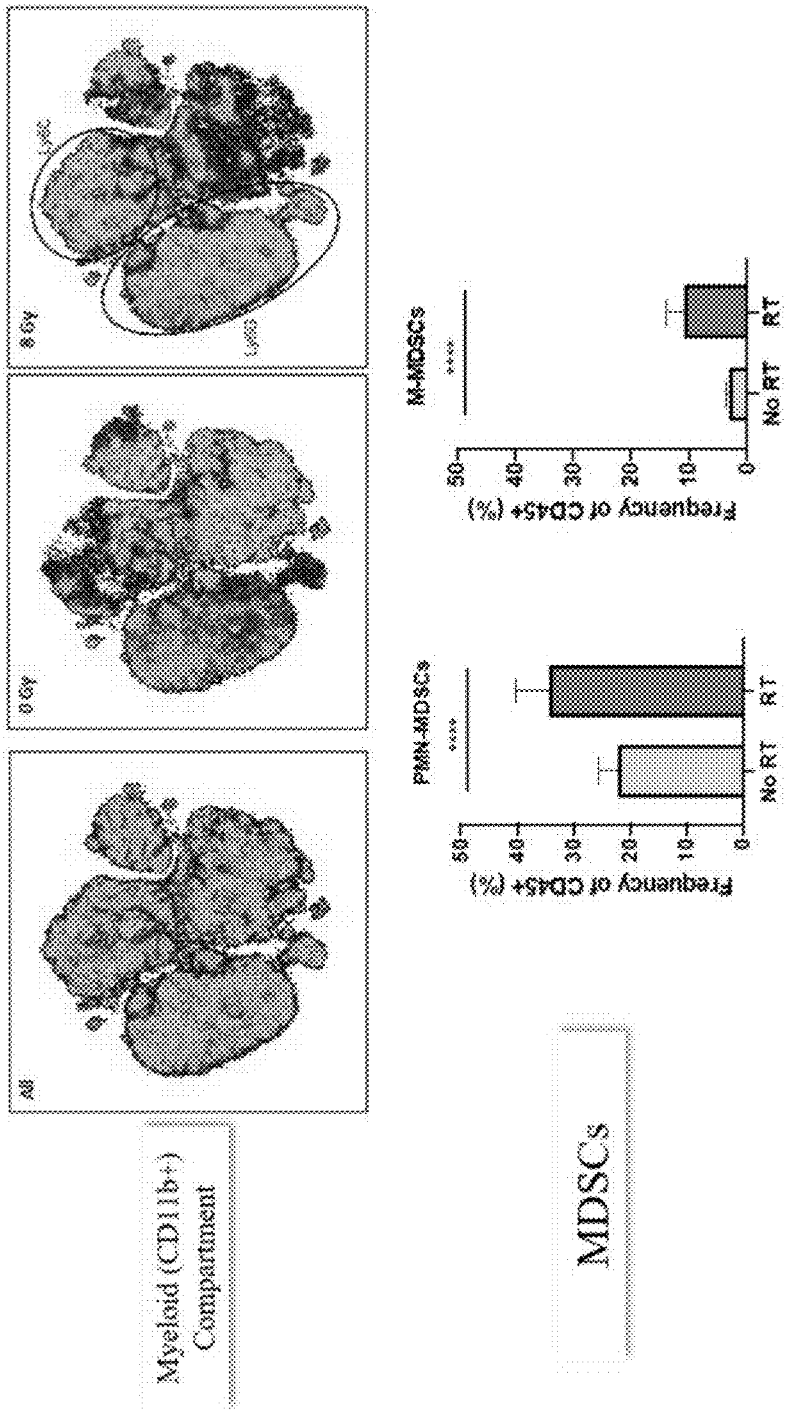
FIG. 16 shows myeloid compartment by t-distributed stochastic neighbor embedding (tSNE).
Figure 17:
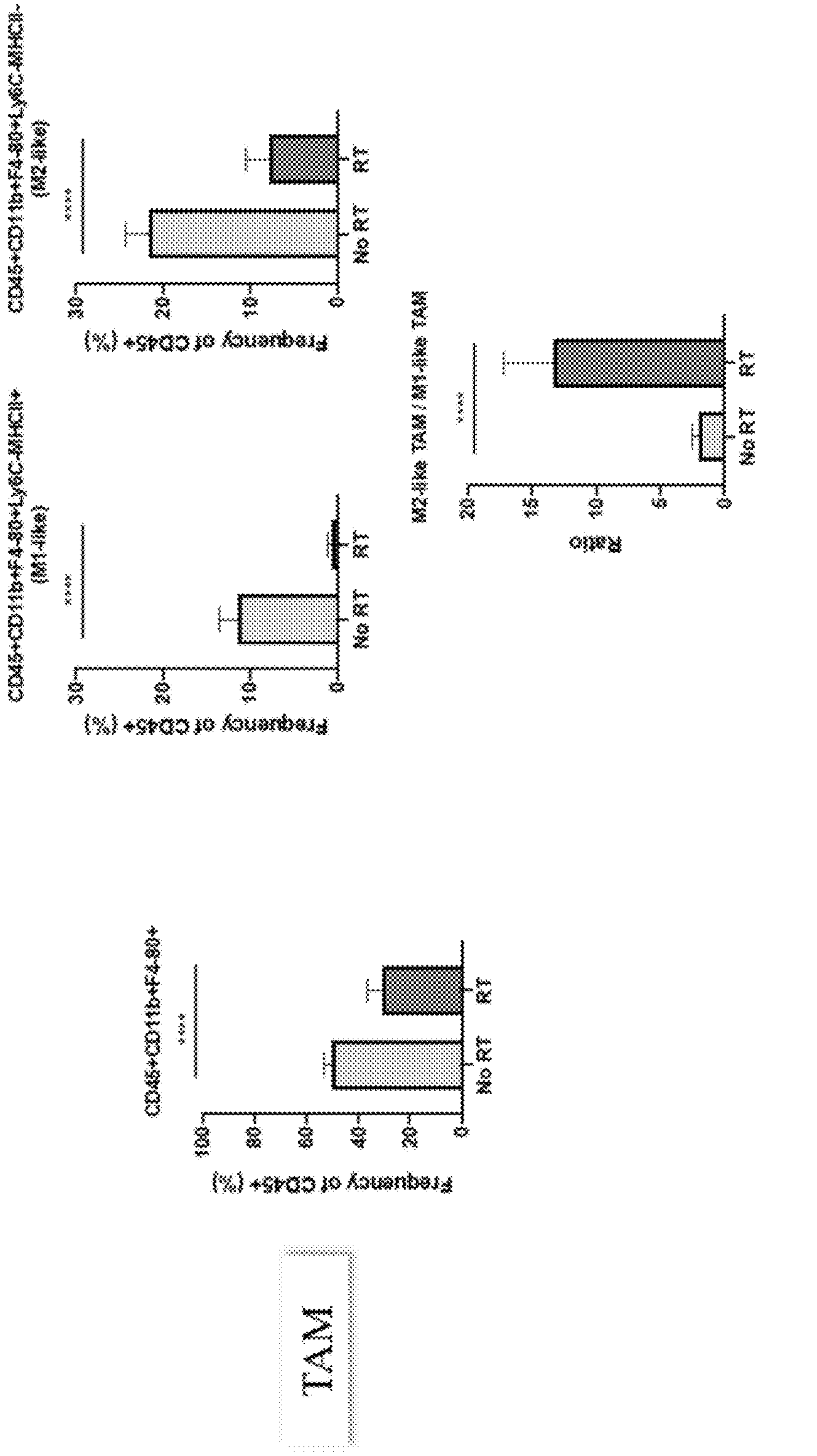
FIG. 17 shows myeloid compartment by tumor-associated macrophage (TAM).
Figure 19:
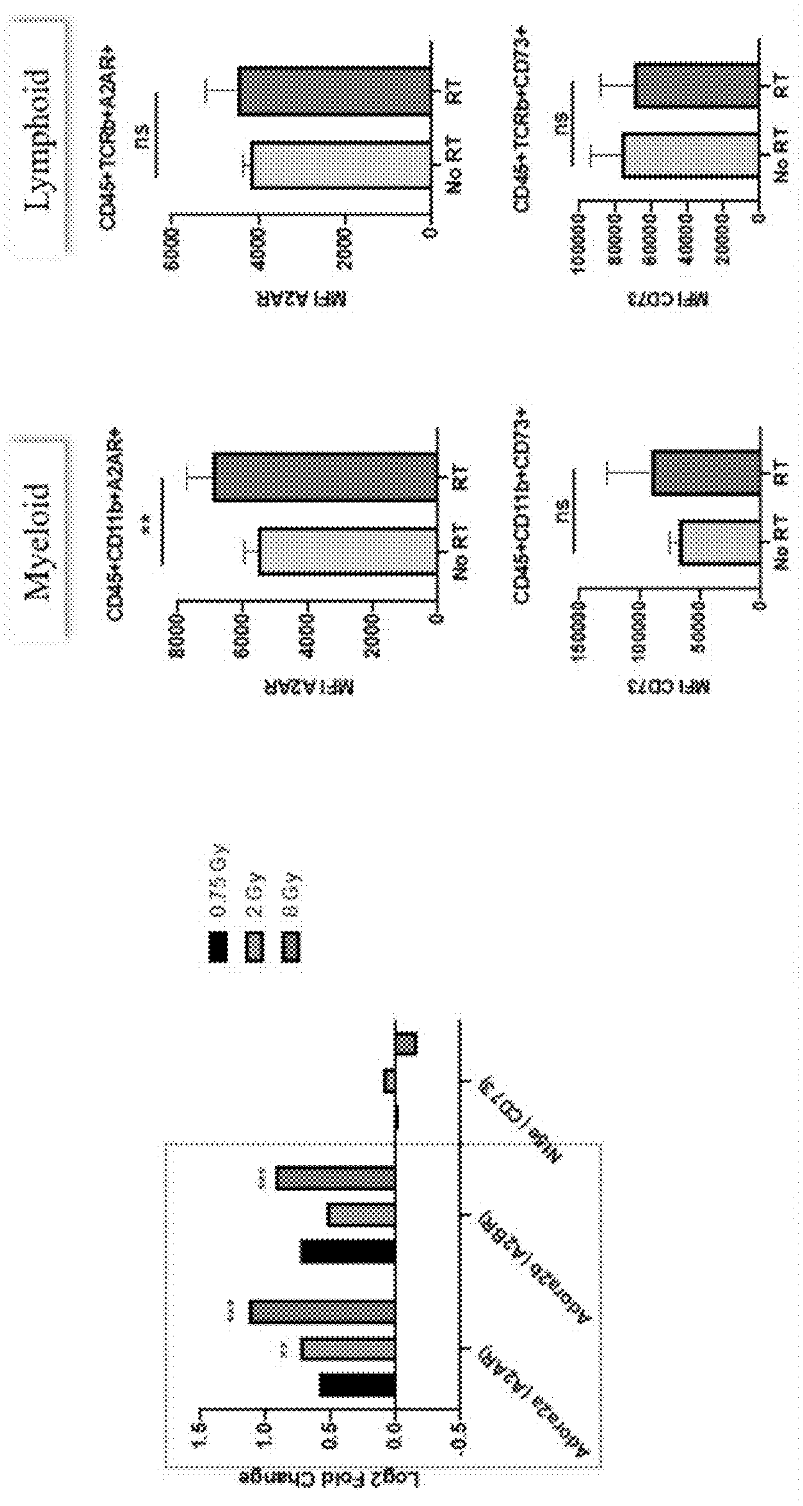
FIG. 19 shows adenosine A2a receptor (A2AR) gene and its cell surface expression.
Figure 20:
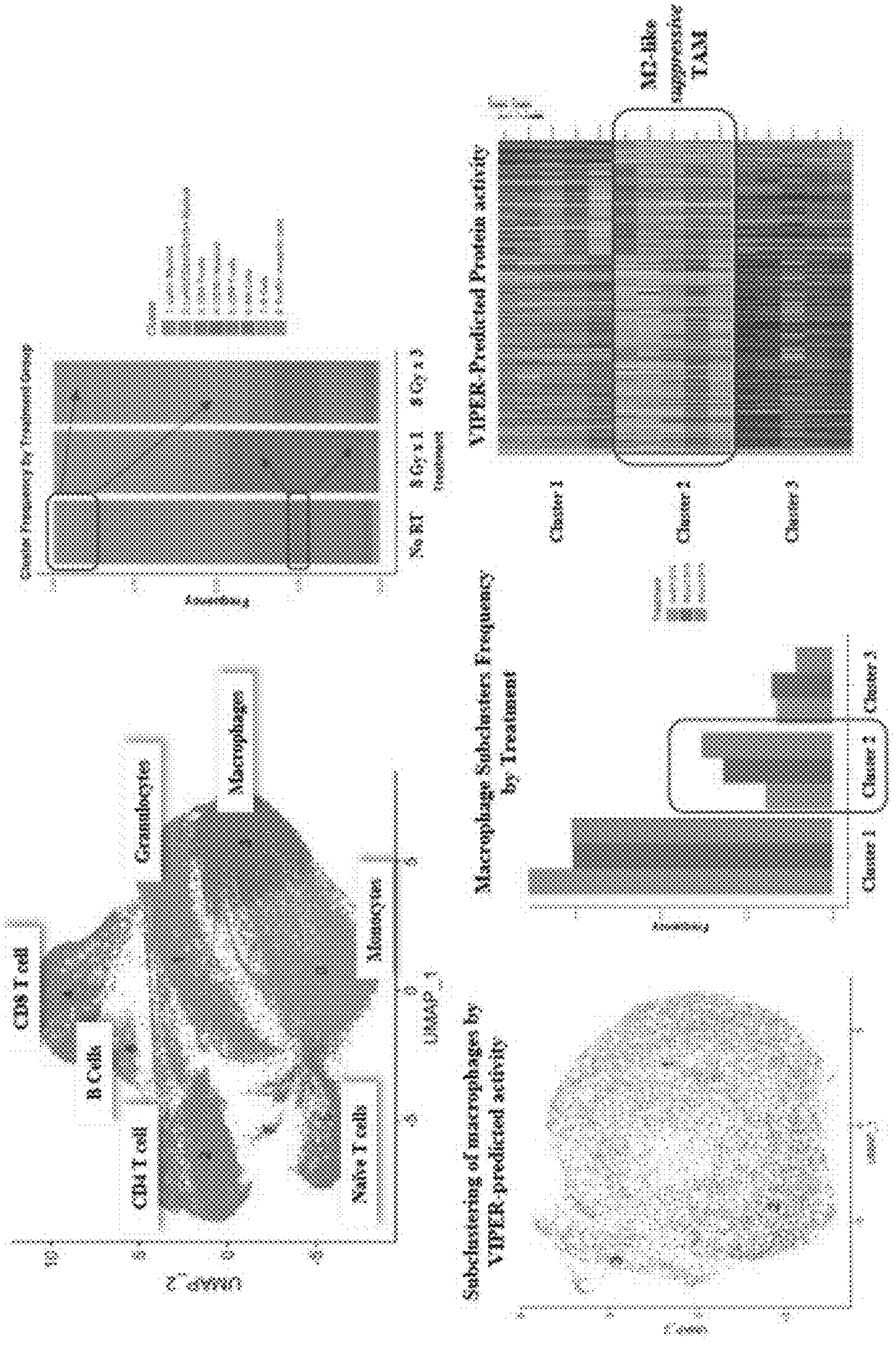
FIG. 20 shows single cell analyses.
Figure 23:
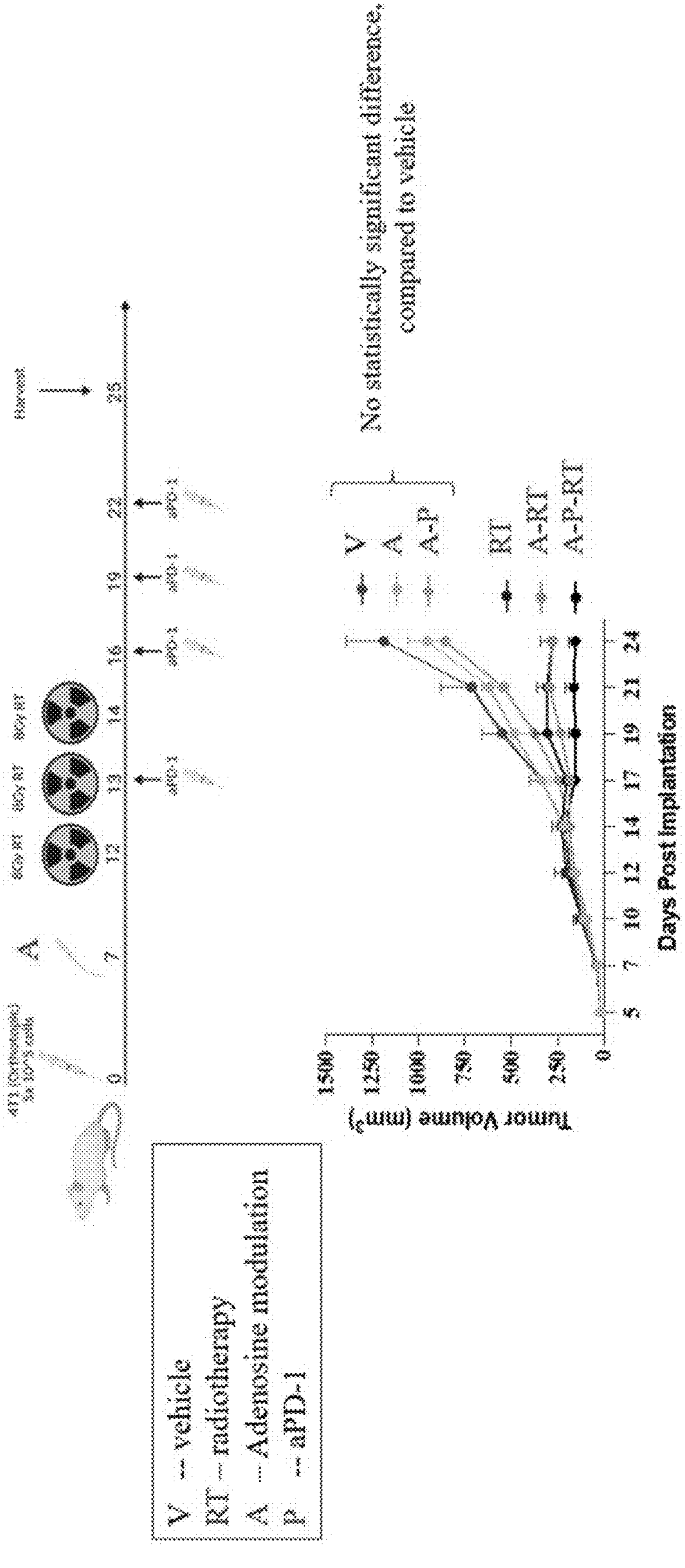
FIG. 23 shows the combination of radiation therapy with immunotherapy and an adenosine signaling modulator.
Figure 24:
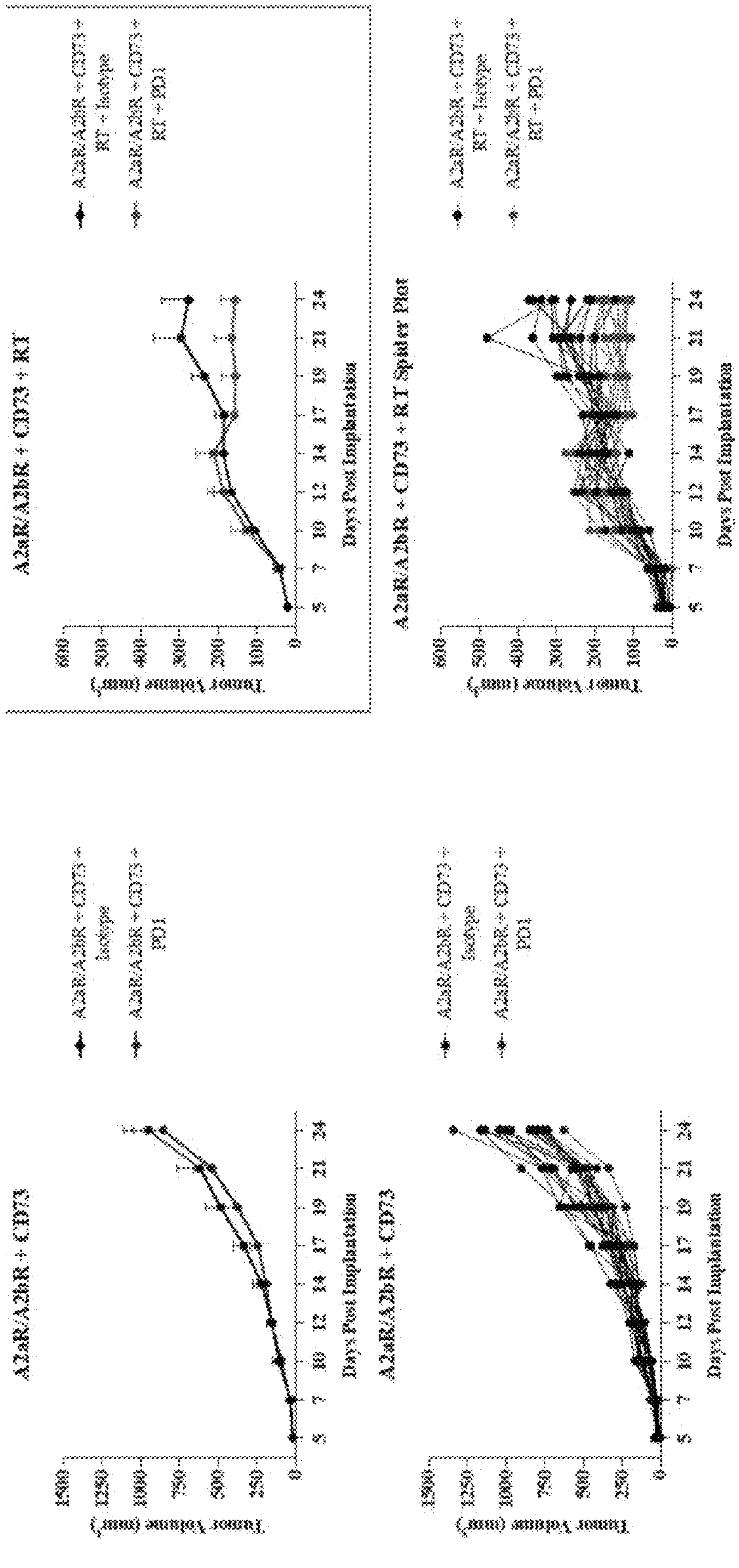
FIG. 24 shows the changes of tumor volume after the combination of radiation therapy with immunotherapy and an adenosine signaling modulator.
Figure 25:
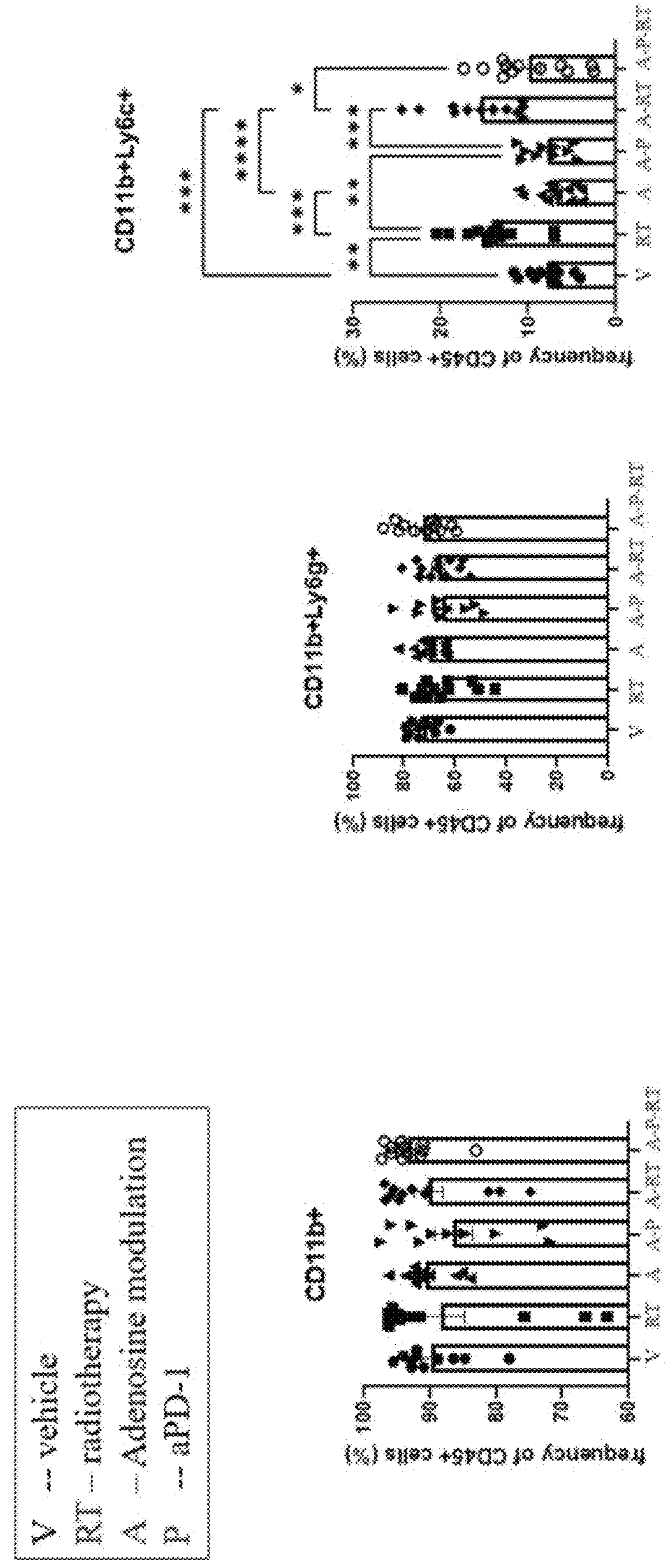
FIG. 25 shows the frequency of CD45+ cells after the combination of radiation therapy with immunotherapy and an adenosine signaling modulator.
Figure 26:
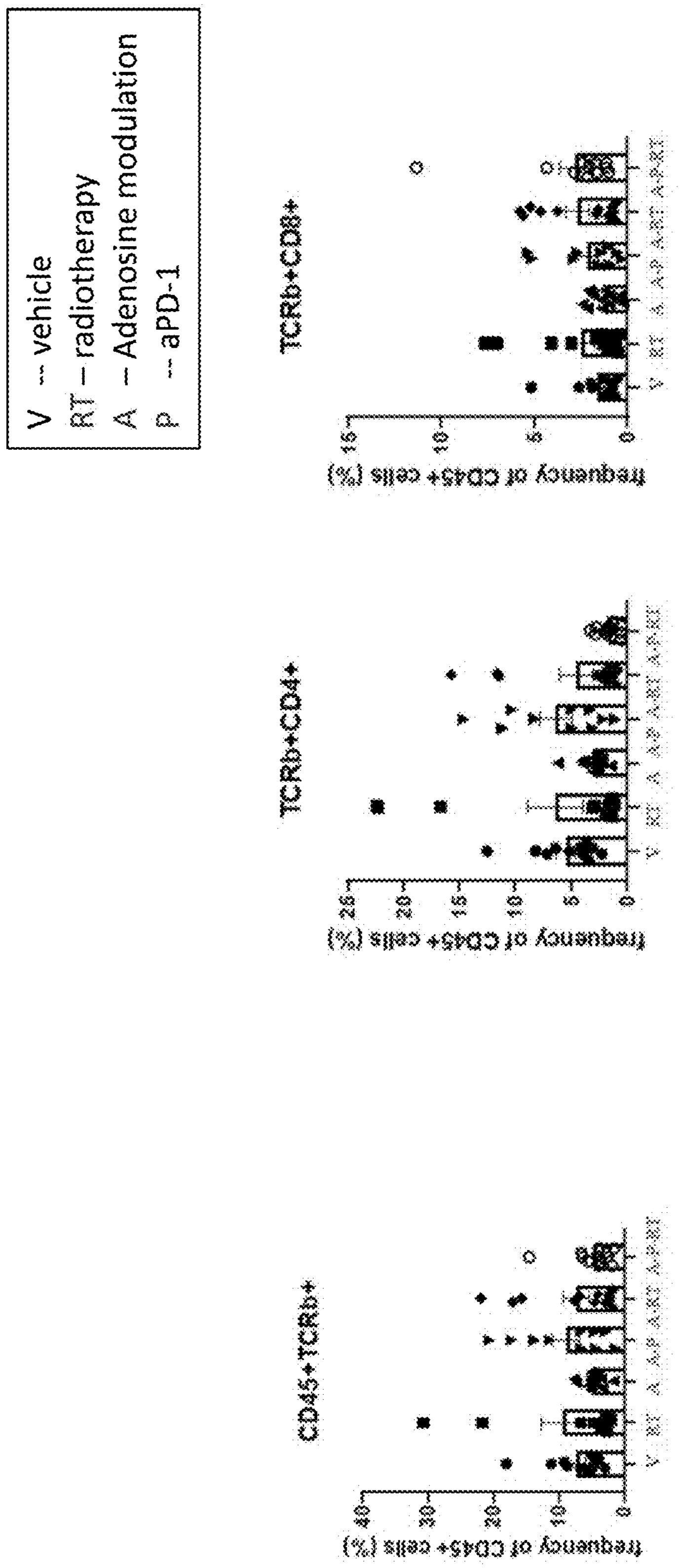
FIG. 26 shows the frequency of CD45+ cells after the combination of radiation therapy with immunotherapy and an adenosine signaling modulator (continued).
Figure 27:
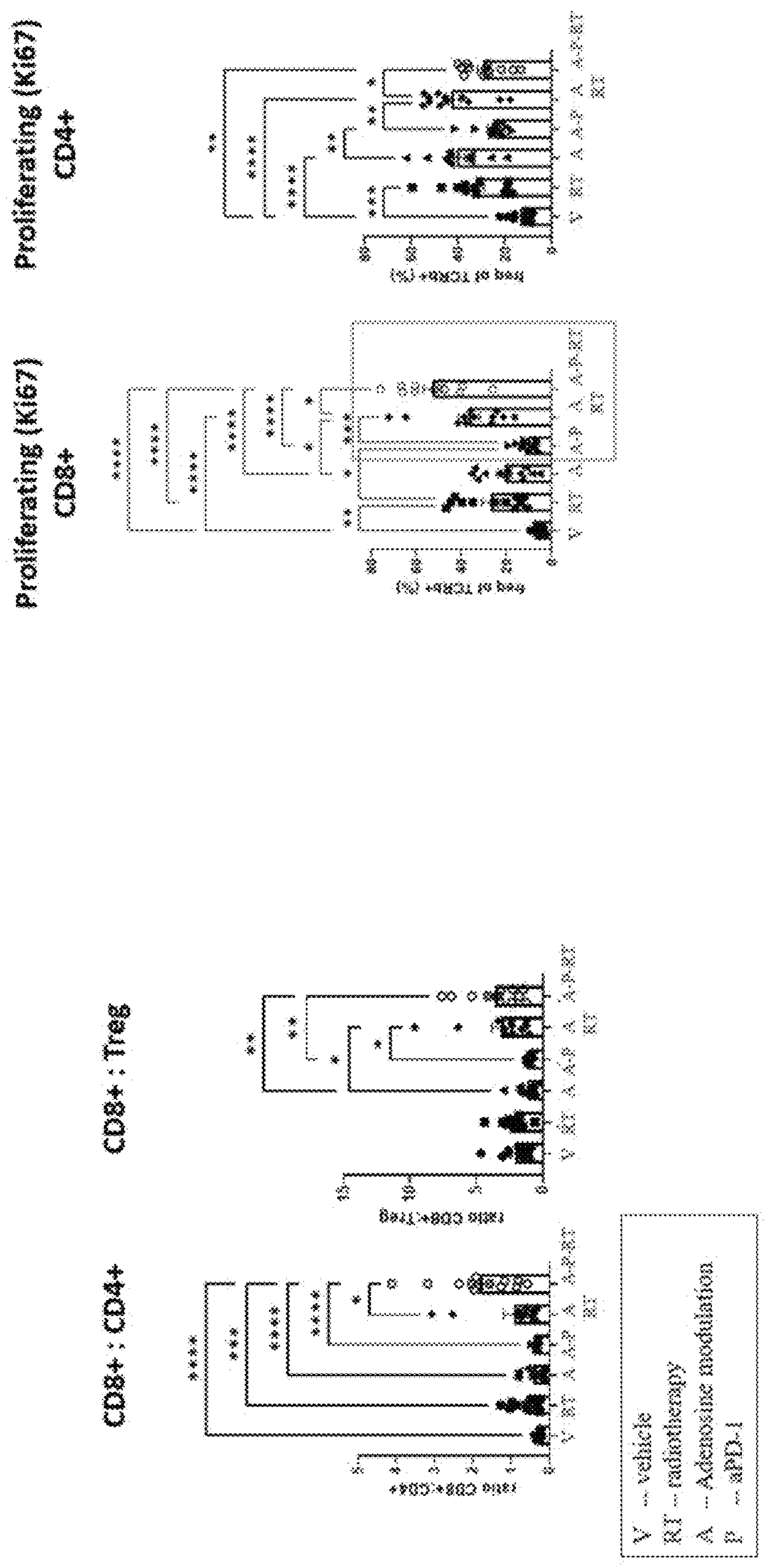
FIG. 27 shows CD4+ and CD8+ cells after the combination of radiation therapy with immunotherapy and an adenosine signaling modulator.
Figure 28:
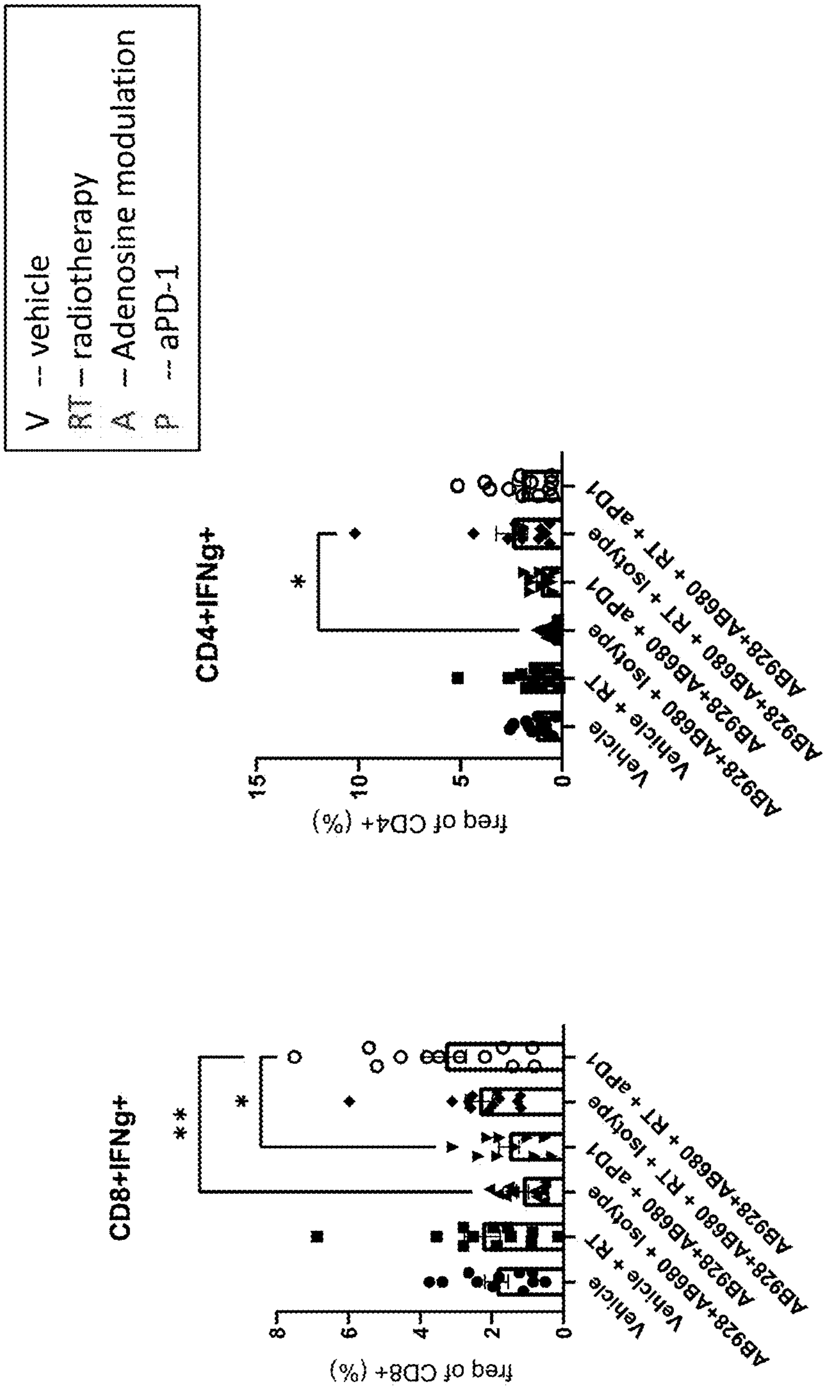
FIG. 28 shows the frequency of CD4+ and CD8+ cells after the combination of radiation therapy with immunotherapy and an adenosine signaling modulator.
Figure 29:
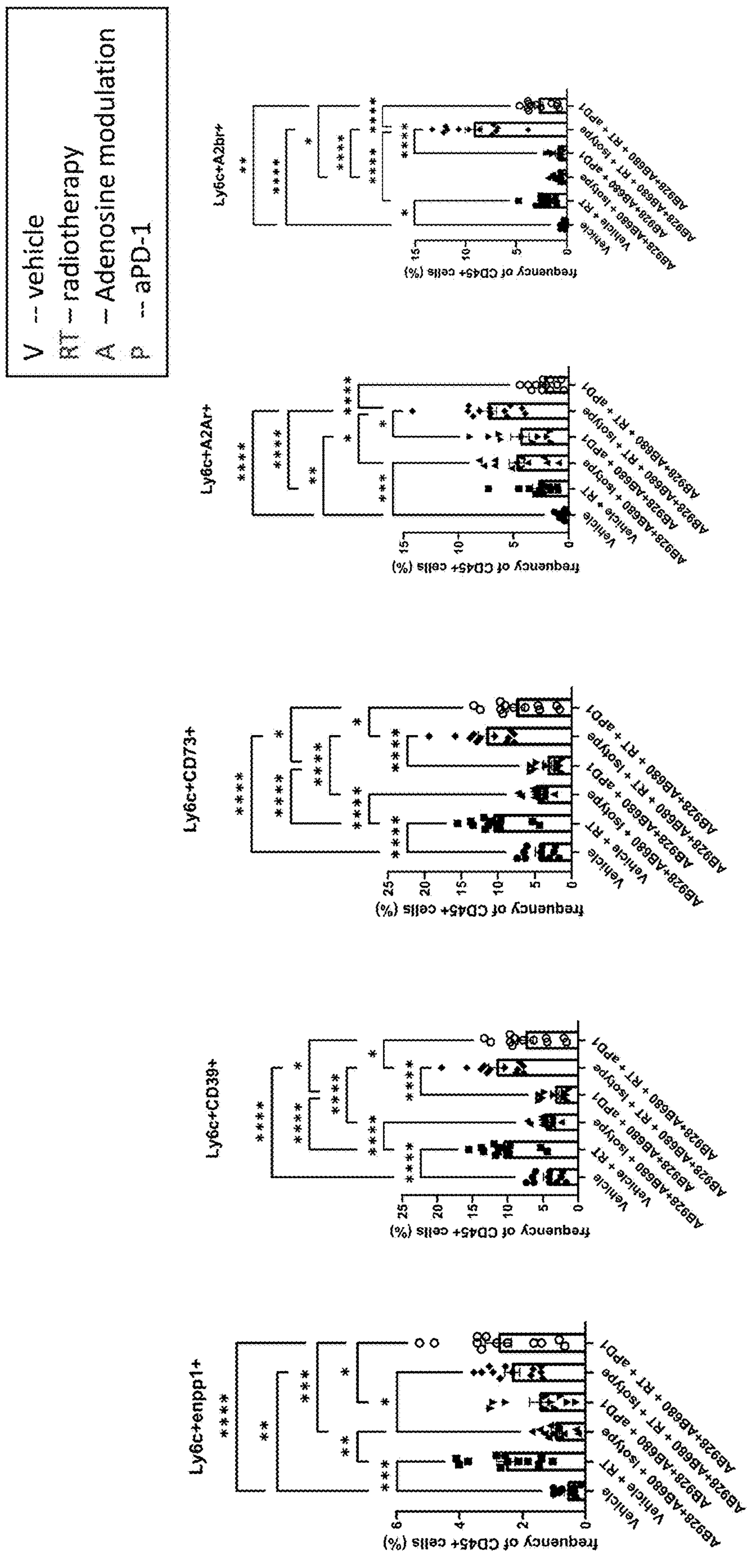
FIG. 29 shows the frequency of CD45+ cells after the combination of radiation therapy with immunotherapy and an adenosine signaling modulator (continued).
Figure 30:
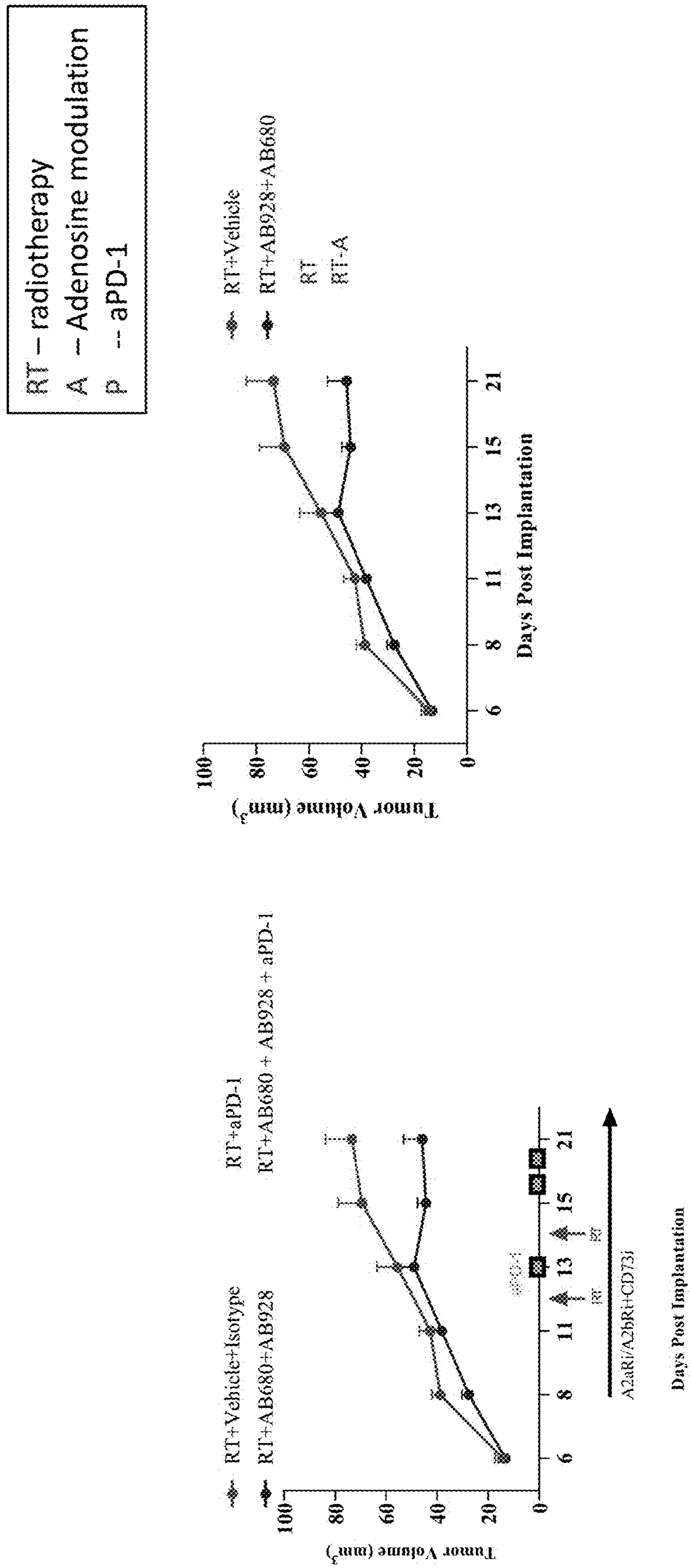
FIG. 30 shows the changes of tumor volume after the combination of radiation therapy with immunotherapy and an adenosine signaling modulator (continued).
Figure 31:
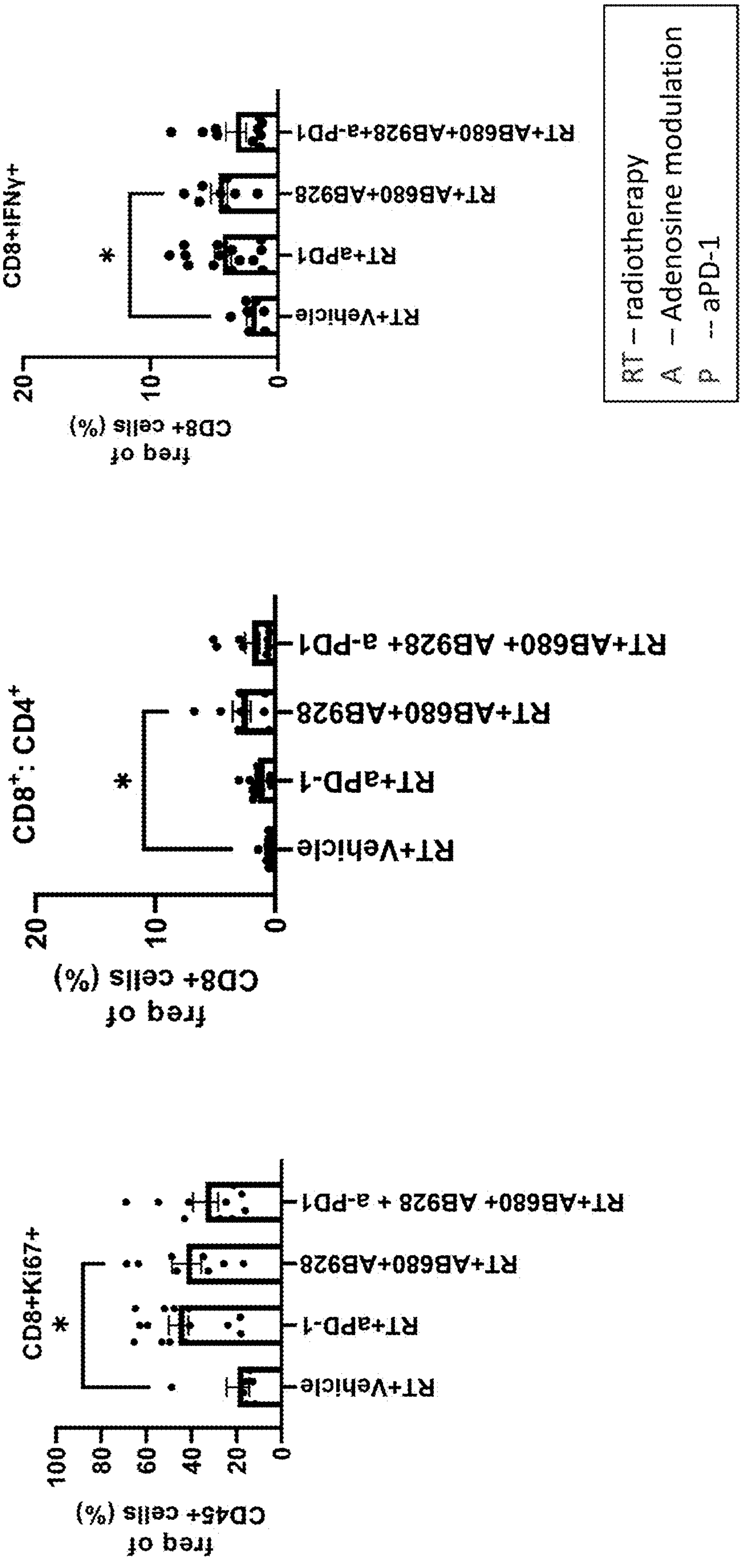
FIG. 31 shows the frequency of CD45+ and CD8+ cells after the combination of radiation therapy with immunotherapy and an adenosine signaling modulator (continued).
Figure 32:
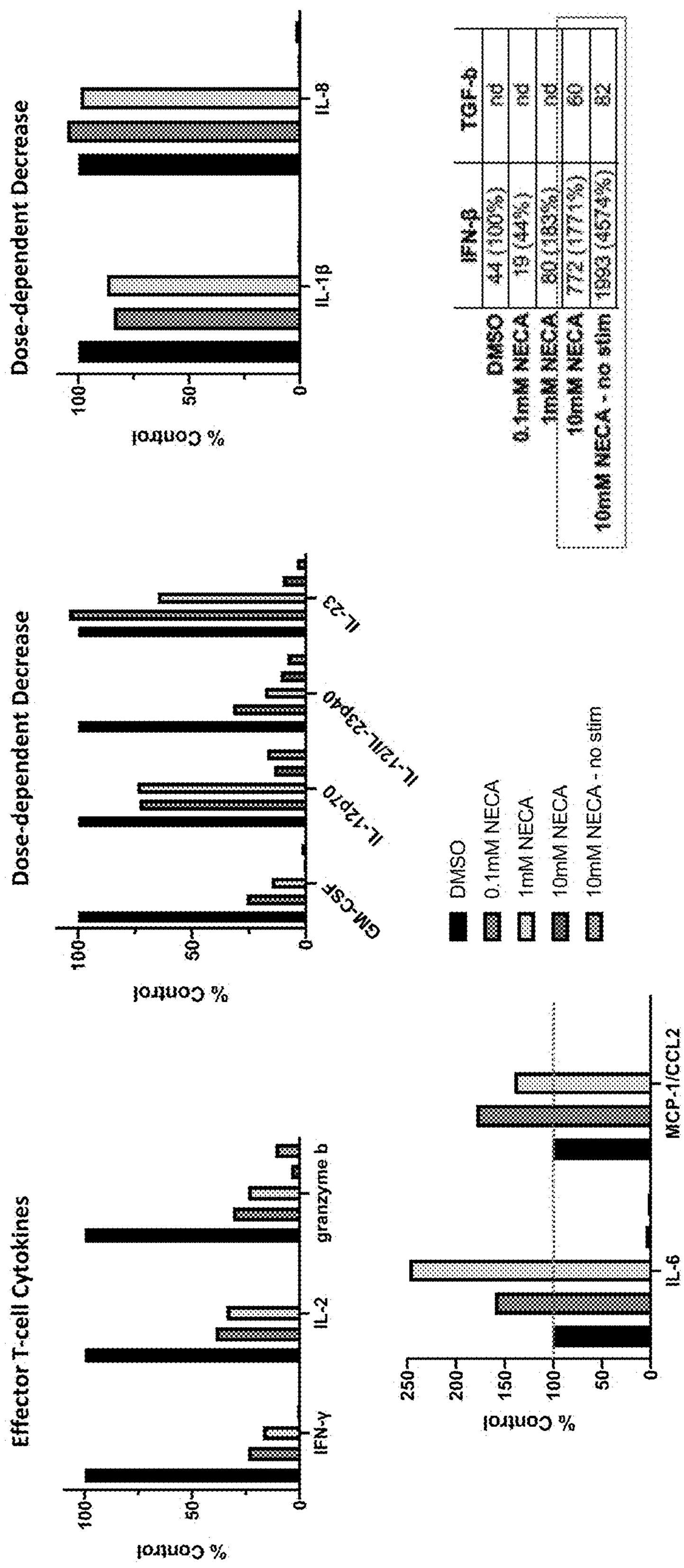
FIG. 32 shows the treatment of human peripheral blood mononuclear cells (PBMCs) with the adenosine signaling modulator 5'-(N-Ethylcarboxyamindo) adenosine (NECA (0.1-10 mM)).
Figures 33A, 33B:
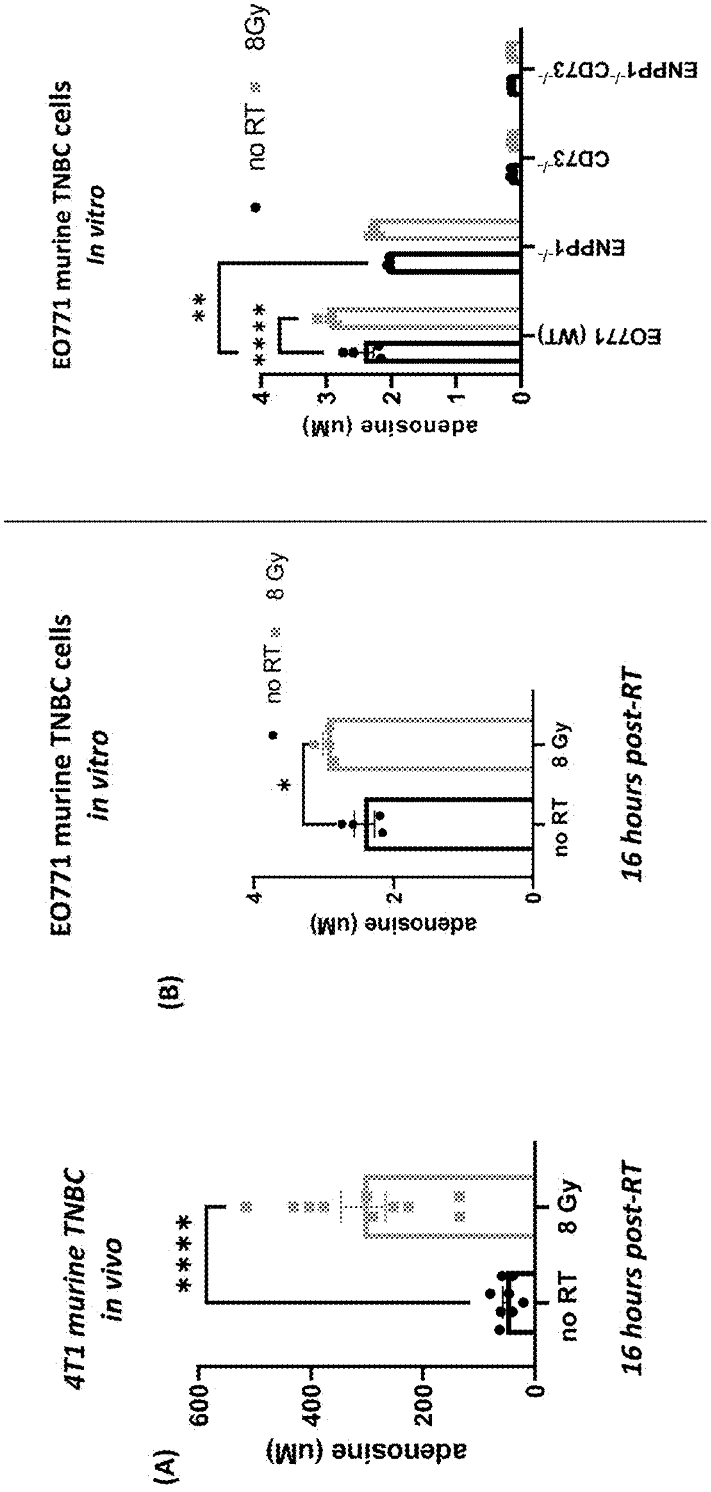
FIGS. 33A-C provide graphs showing that radiotherapy increases (FIG. 33A) intra-tumoral adenosine in 4T1 orthotopic murine TNBC tumors in vivo and (FIG. 33B) EO771 murine TNBC cells in vitro.
Figure 33C:
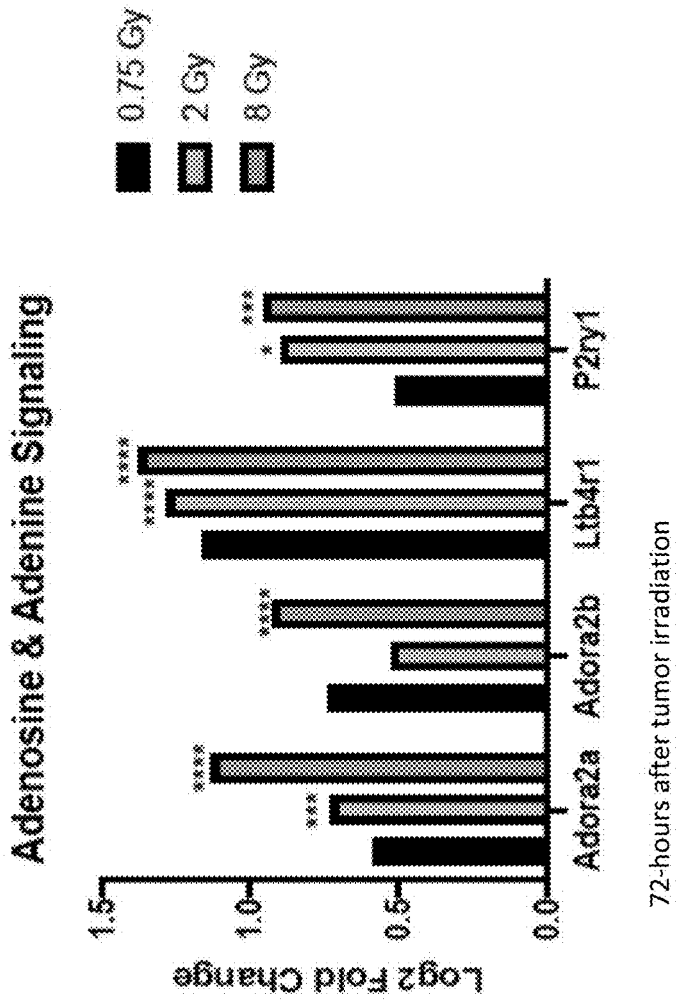
Figures 34A, 34B:
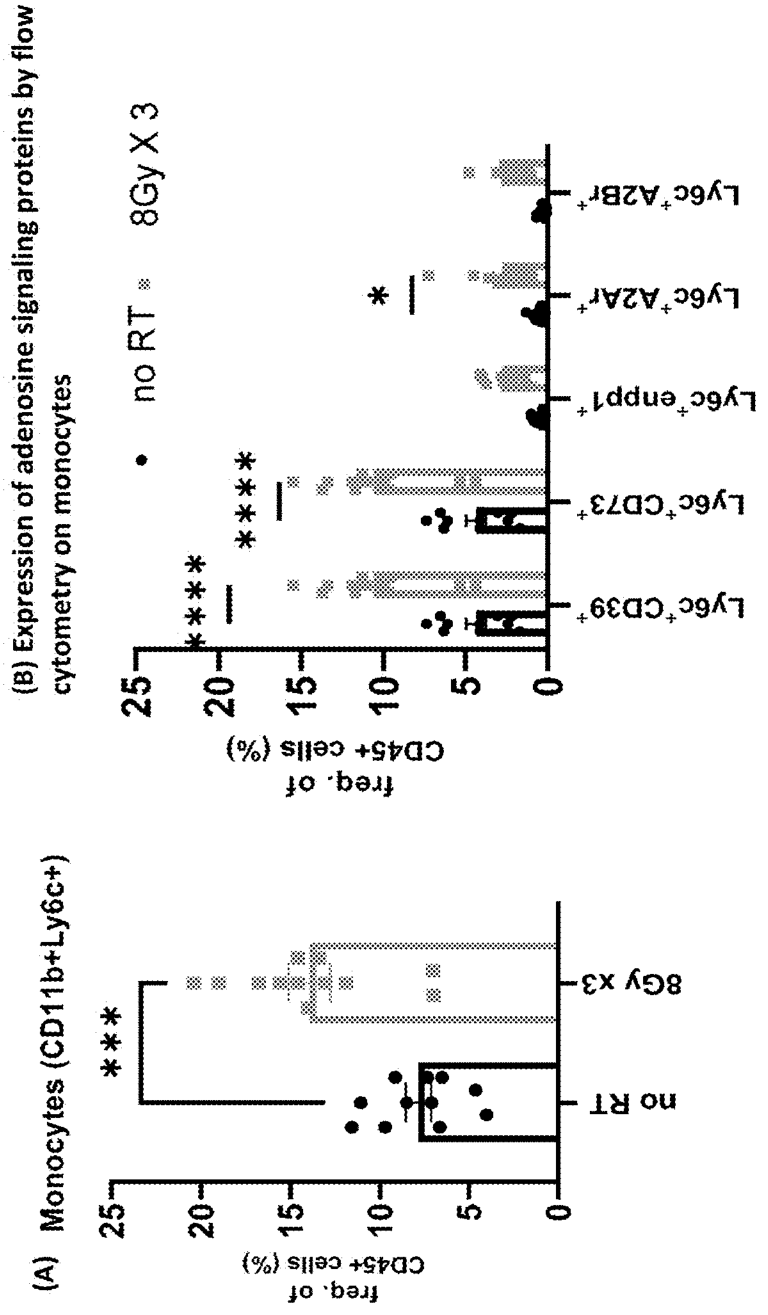
FIGS. 34A-C provide graphs illustrating that radiotherapy increases (FIG. 34A) abundance of intratumorally monocytes, (FIG. 34B) expression of adenosine signaling genes on monocytes in 4T1 tumors and (FIG. 34C) expression of adenosine signaling proteins by flow cytometry on T cells.
Figure 34C:
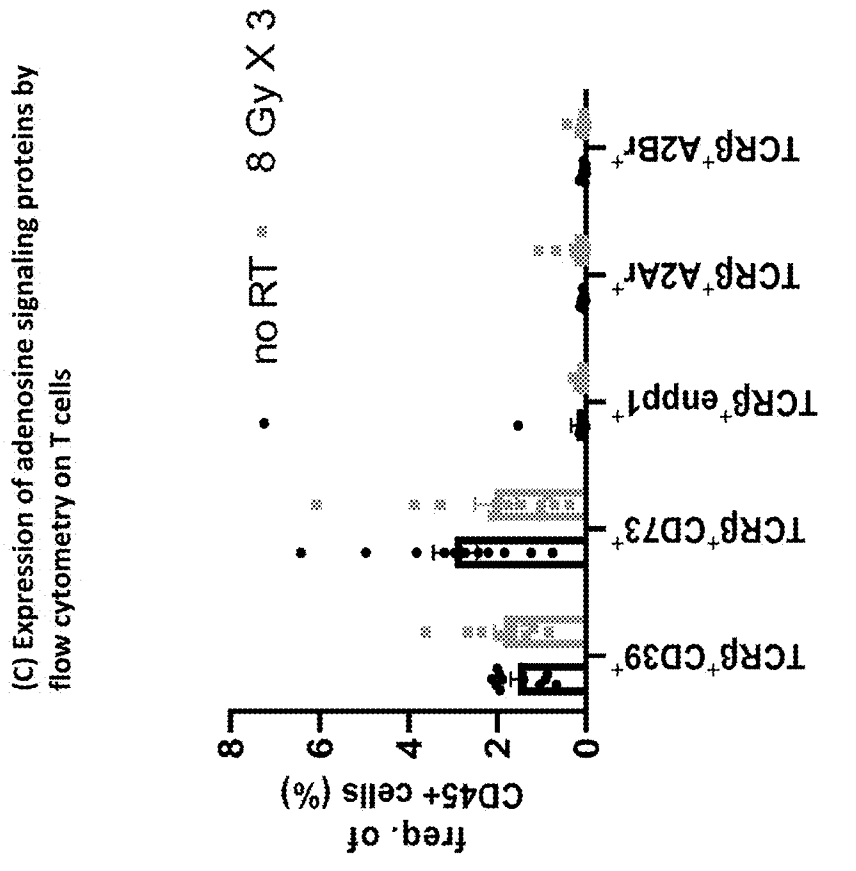
Figures 35A, 35B:
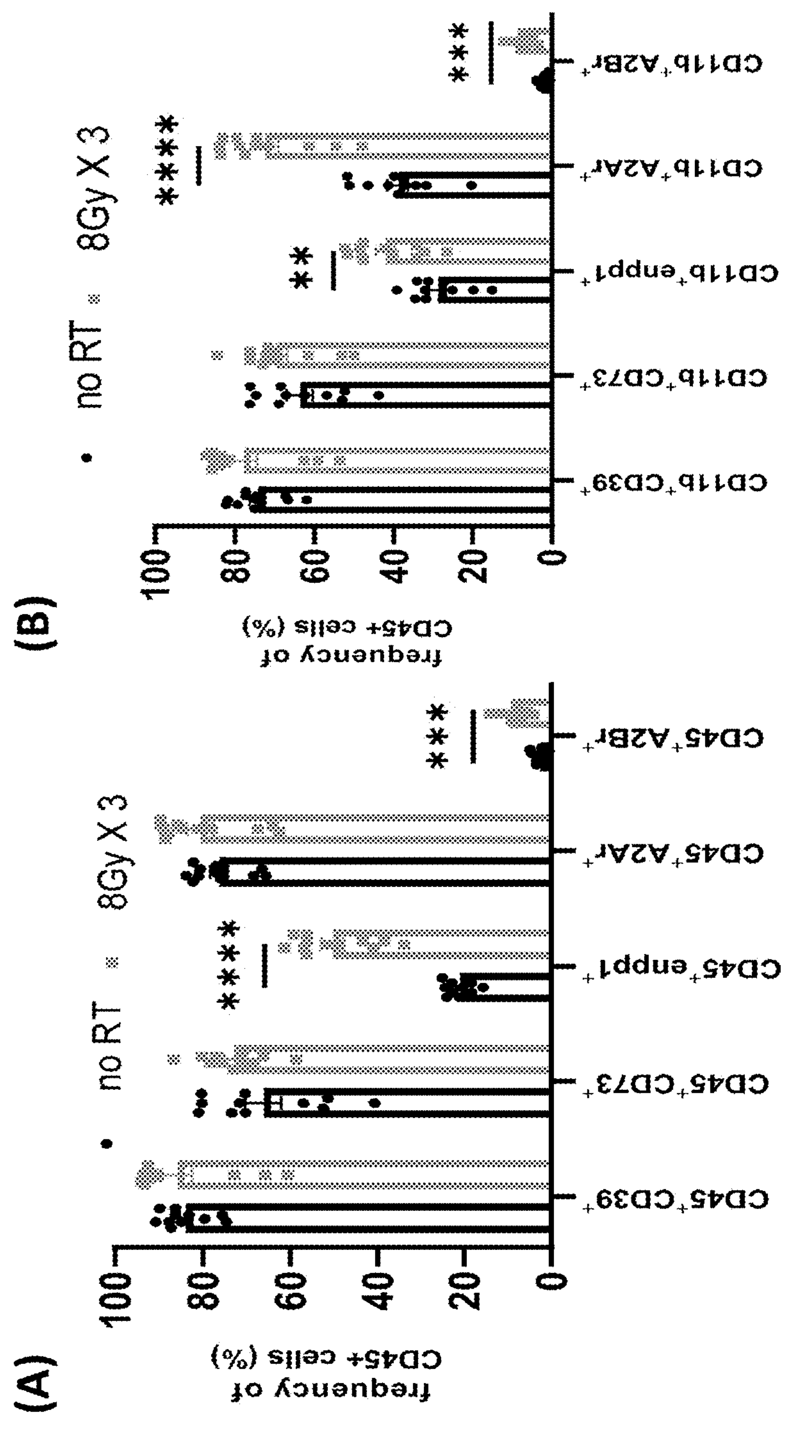
FIGS. 35A-C provide graphs showing that radiotherapy differentially increases expression adenosine signaling proteins on (FIG. 35A) CD45+ immune compartment, (FIG. 35B) CD11b myeloid cells and (FIG. 35C) granulocytes.
Figure 35C:
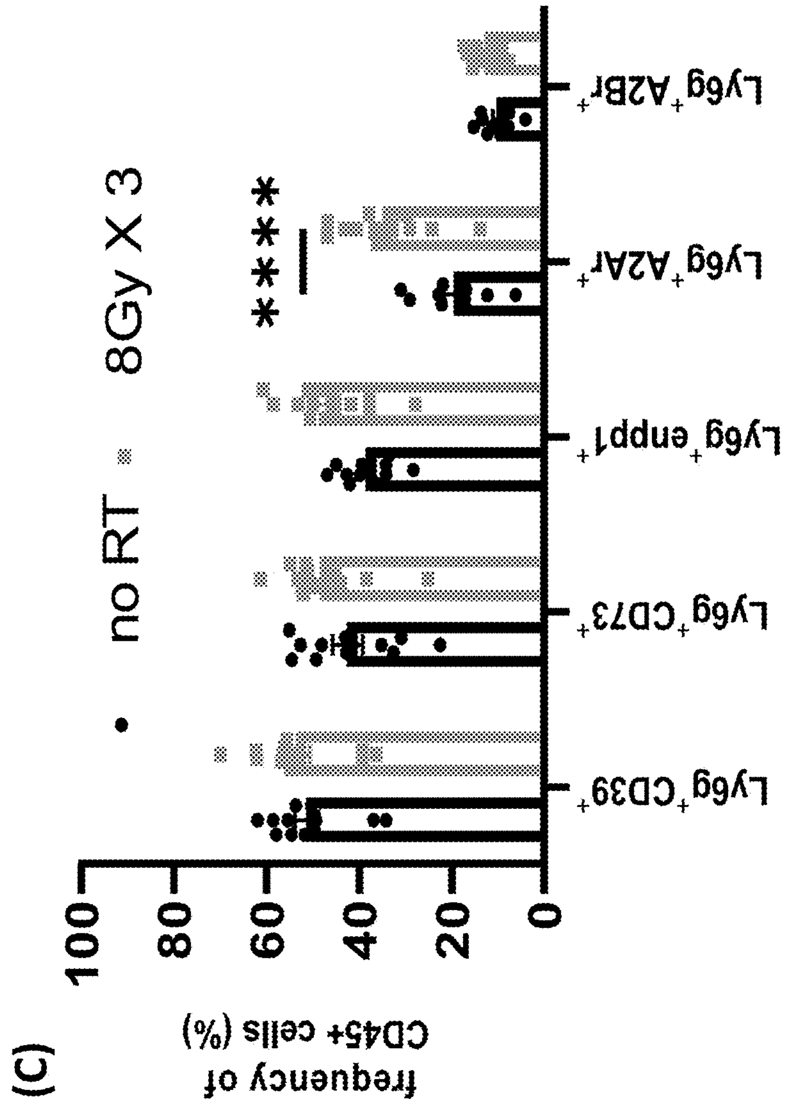
Figures 36A, 36B:
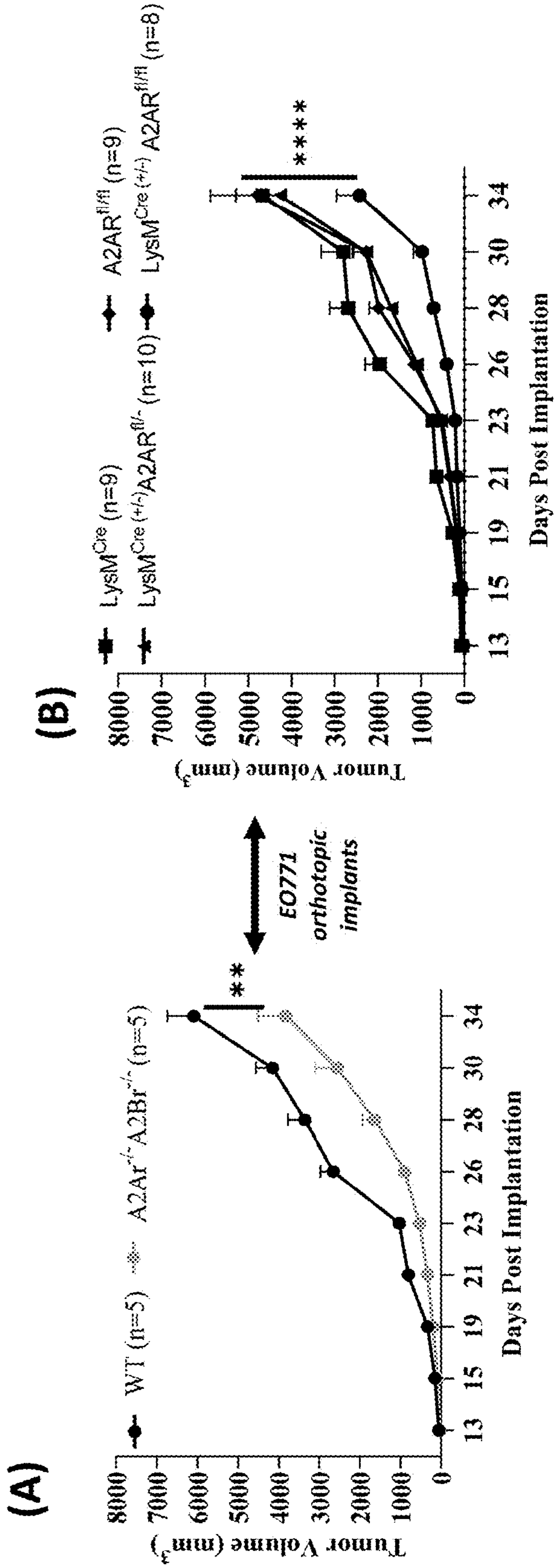
FIGS. 36A-B provide graphs of tumor volume as a function of days post implantation. The results show (FIG. 36A) that whole body knock down of adenosine receptor expression improves control of orthoptic tumors in mice and (FIG. 36B) knockdown of A2AR in the myeloid compartment alone significantly improves tumor control.
Figures 37A, 37B:
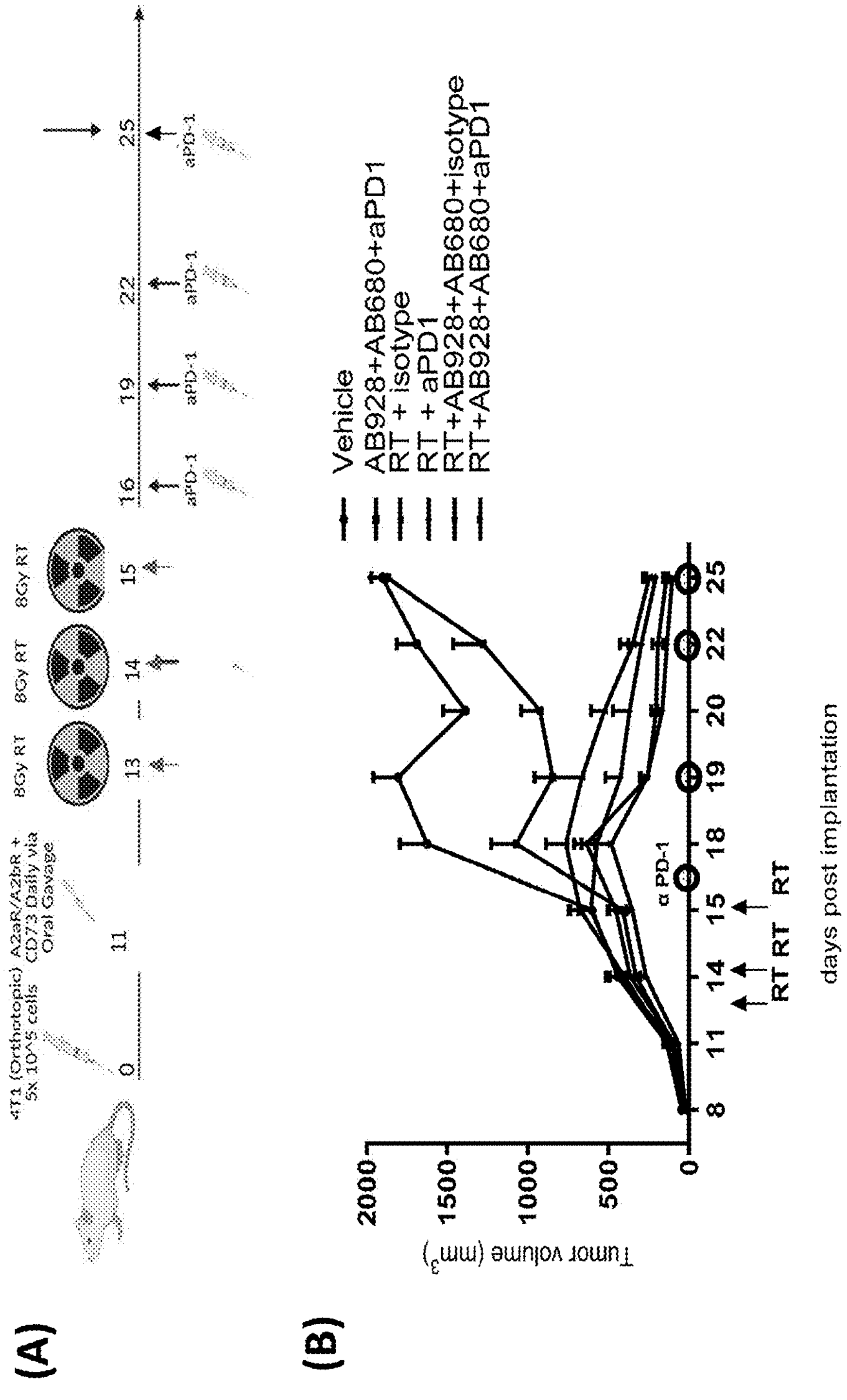
FIGS. 37A-B illustrate that radiotherapy improves tumor control by improving efficacy of adenosine signaling inhibitor and aPD-1.
Figures 38A, 38B, 38C, 38D:
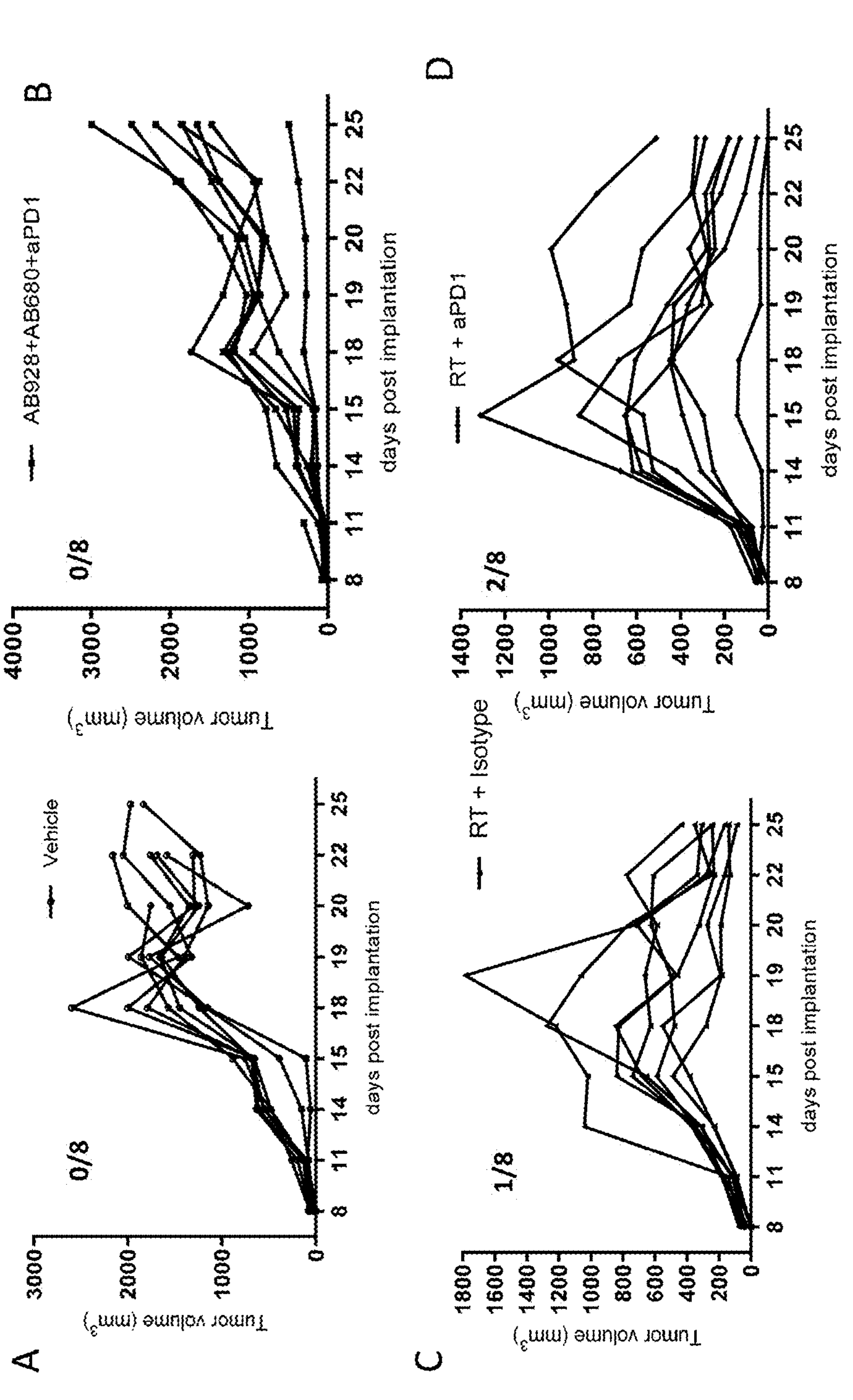
FIGS. 38A-F provides additional test results showing that radiotherapy improves tumor control by improving efficacy of adenosine signaling inhibitor and aPD-1.
Figures 38E, 38F:
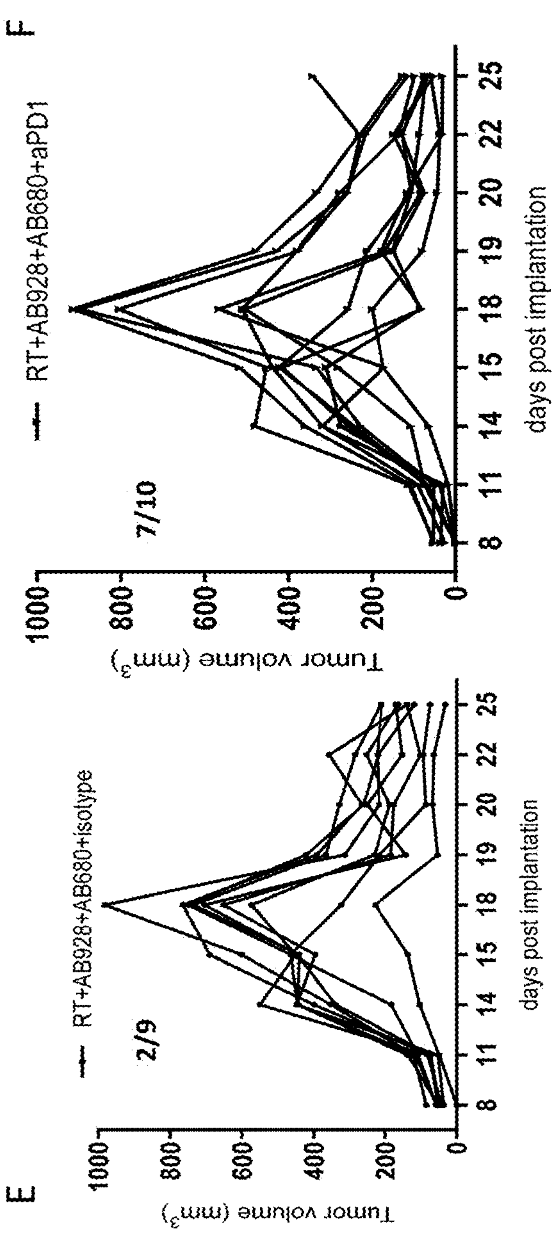
Figure 39:
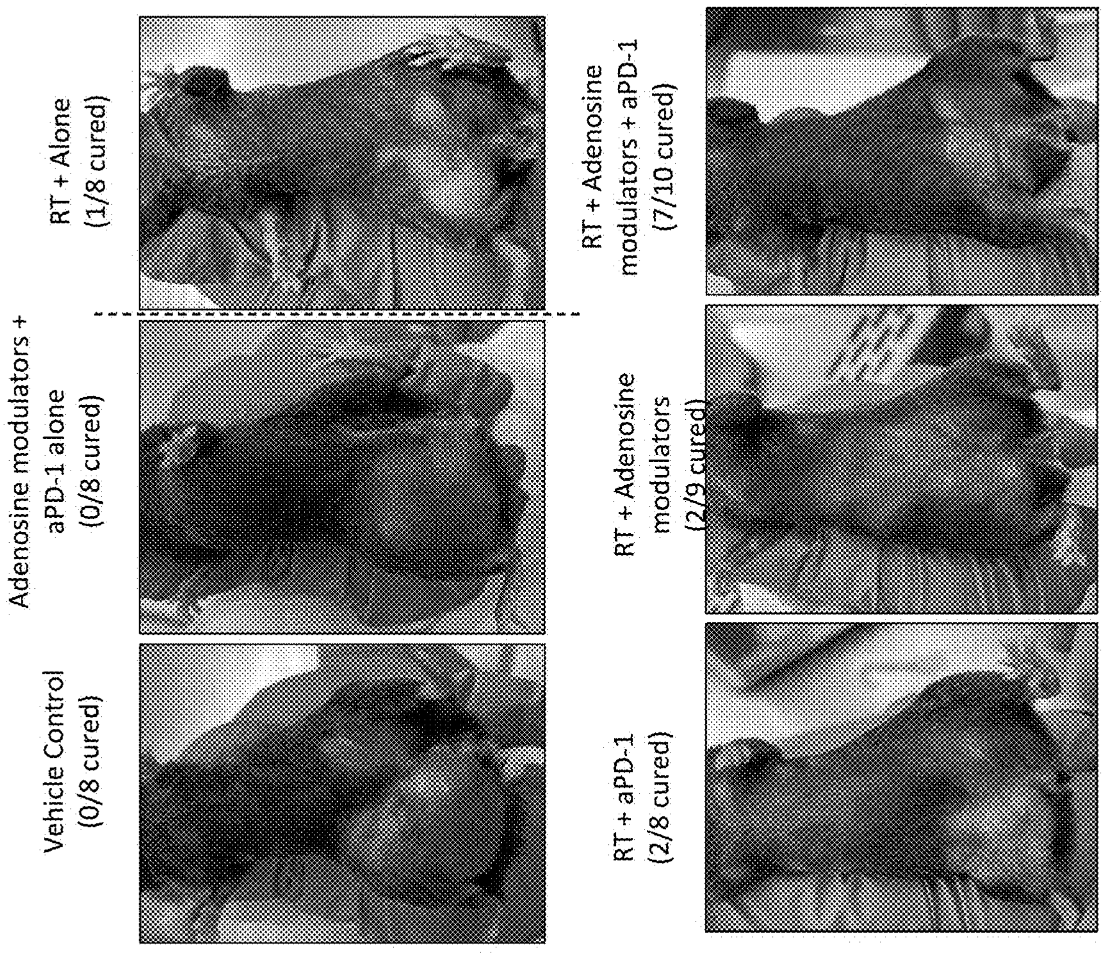
FIG. 39 provides photographs of test mice illustrating results for various treatments using one or more of tumor irradiation, adenosine signaling modulators, and checkpoint inhibition in murine E0771 breast cancer model (Day 24 post-tumor implantation).
Figures 40A, 40B:
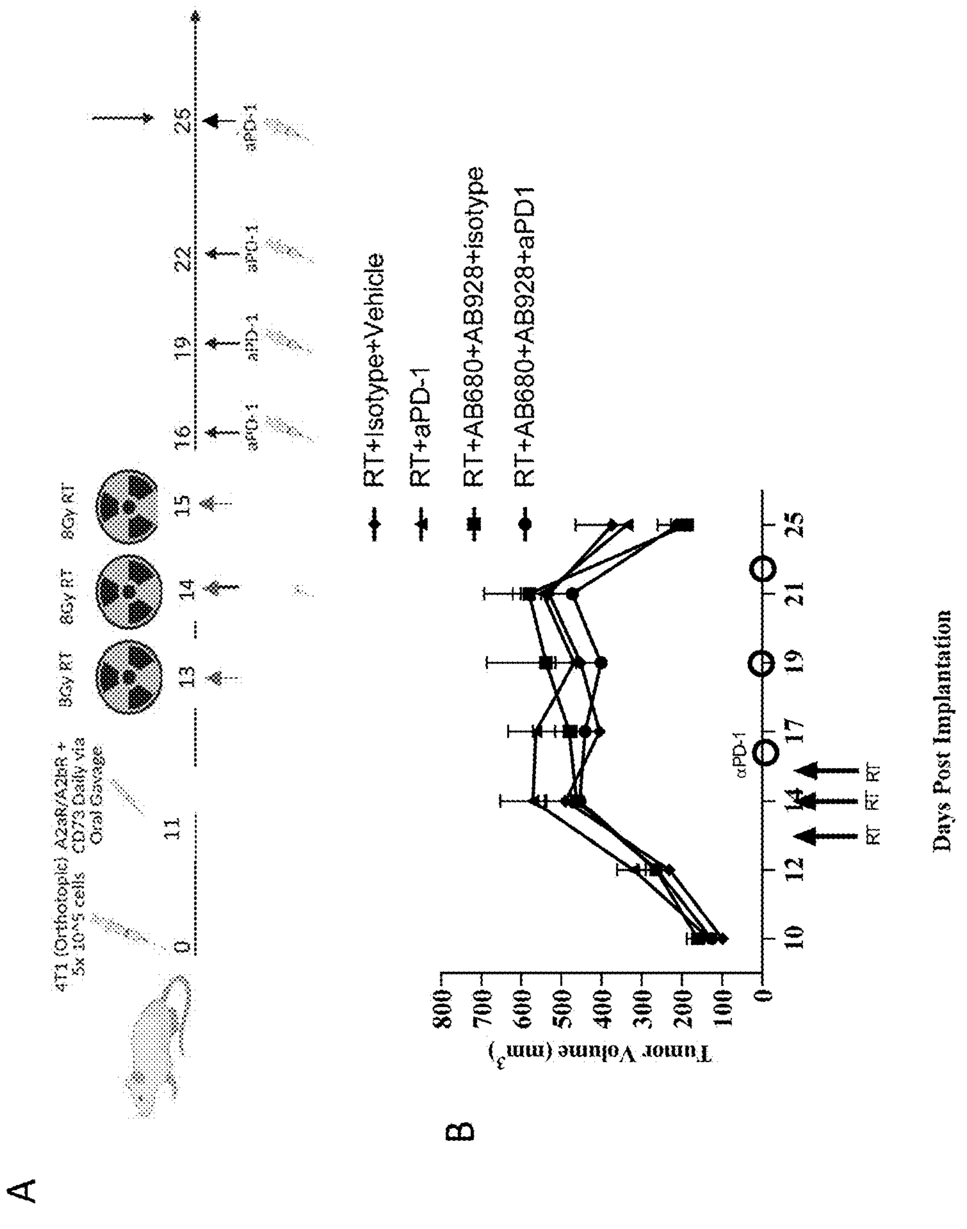
FIG. 40A shows one example of a treatment protocol over time in and FIG. 40B is a graph showing changes in tumor volume over time for various treatments.
Figures 41A, 41B:
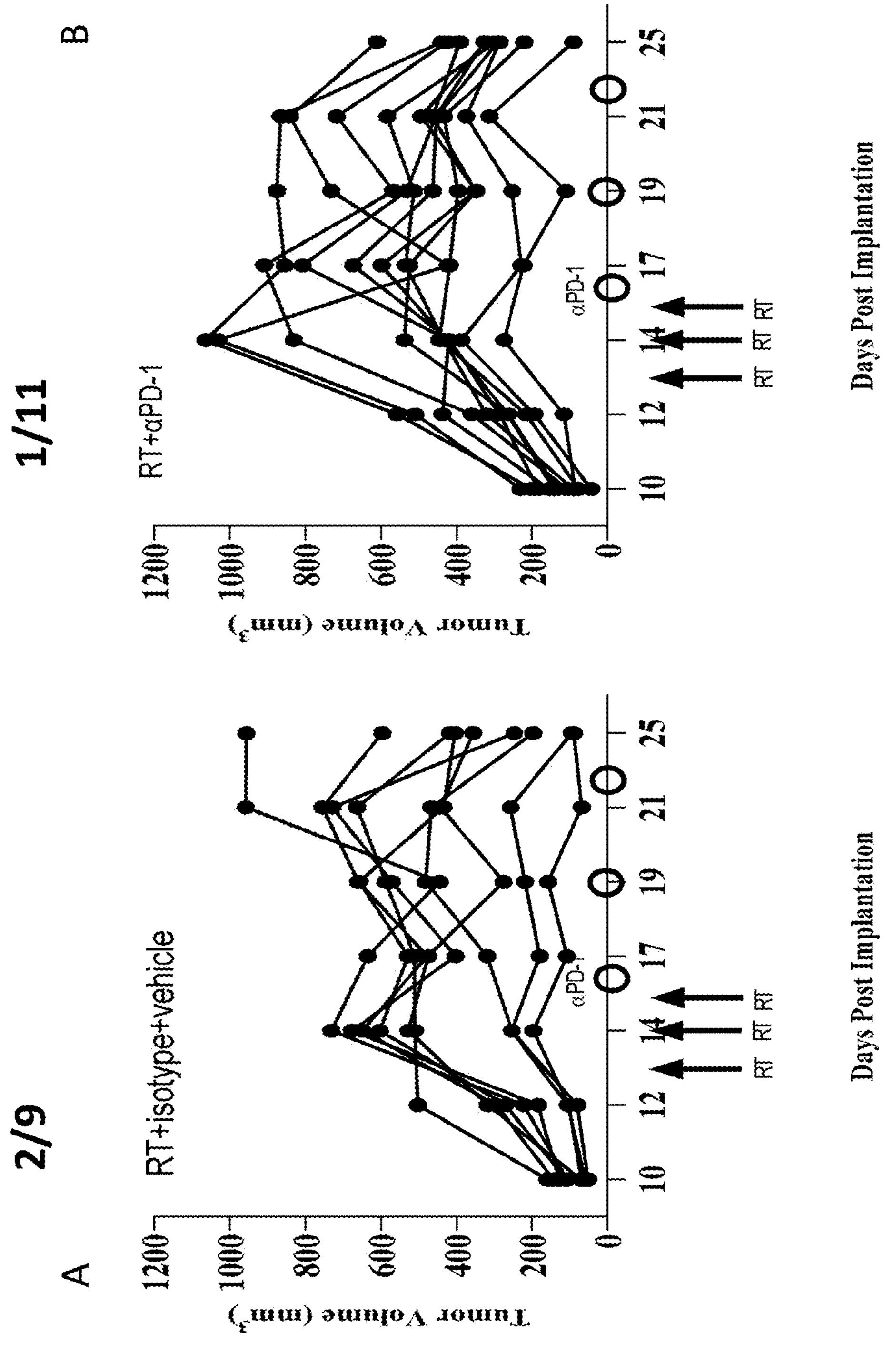
FIG. 41A to FIG. 41D are graphs showing changes in tumor volume over time for various treatments.
Figures 41C, 41D:
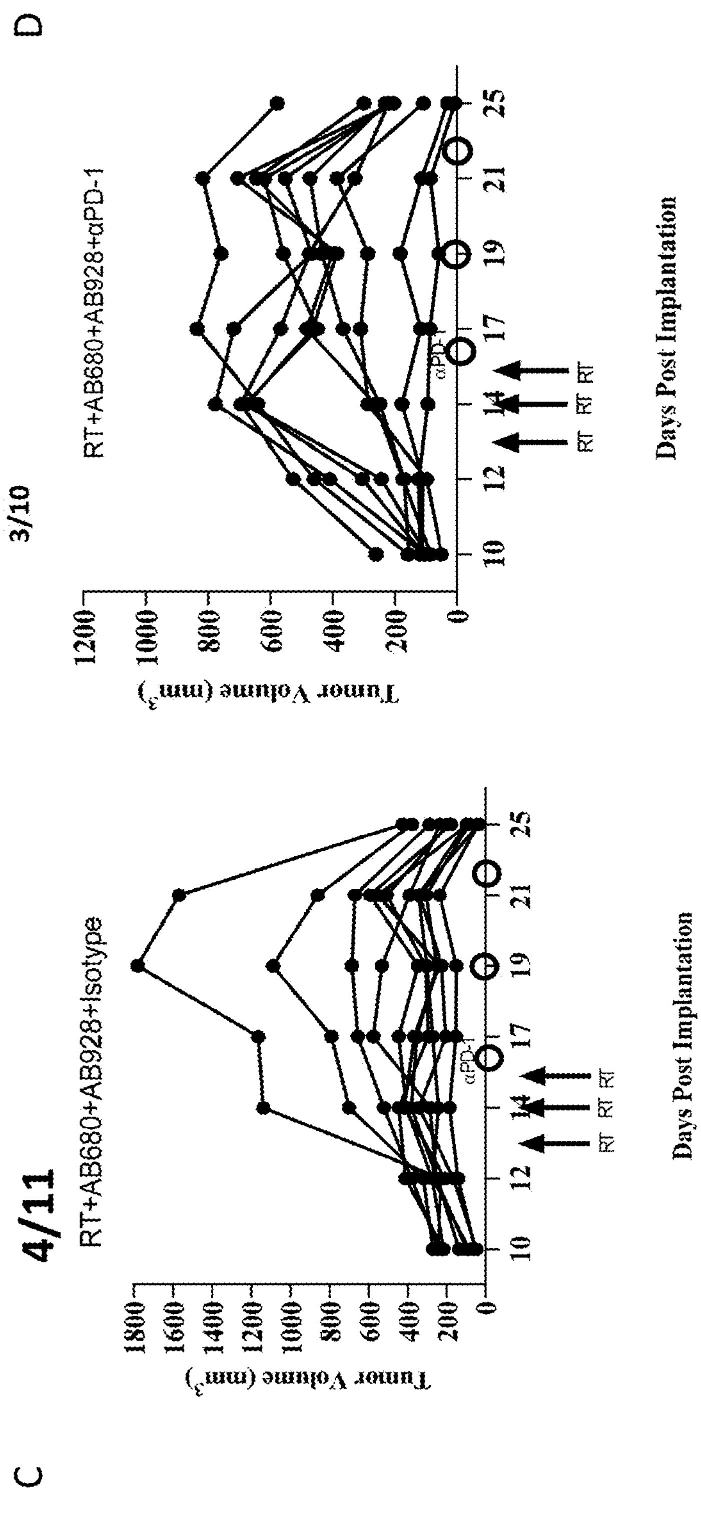

In the 4T1 orthotopic breast cancer spontaneous metastasis mouse model, the breast tumor cells are transplanted into the mammary fat pad to establish primary tumor nodules. The primary tumor can then be surgically removed as in human breast cancer patients. 4T1 tumor cells are highly invasive. Almost all tumor-bearing mice develop metastasis in 30 days after tumor transplant into the mammary fat pad. 4T1 tumors grow aggressively in the primary sites. Using a preclinical 4T1 orthotopic breast cancer mouse model is shown in FIG. 13.

Myeloid populations were defined by flow cytometry based on the following immunophenotypic analyses:

Immunosuppressive TAM: CD45+CD11b+F4-80+MHCII-Ly6C- and CD45+CD11b+F4-80+MHCII-Ly6C-Arg+

Pro-inflammatory TAM: CD45+CD11b+F4-80+MHCII+Ly6C-

Monocytic MDSCs (M-MDSC): CD45+CD11b+F4-80-Ly6C+Ly6G-

Polymorphonuclear MDSC (PMN-MDSC): CD45+CD11b+Ly6C (intermediate) Ly6G+

Finally, leveraging the immuno-oncology tissue processing platform (tumor from OR to lab to immediate processing), the adenosine signaling modulator can be studied in paired irradiated and unirradiated tumor tissue by scRNASeq, cytokine analyses, or qmIF. The preclinical tools can be used to understand the implications of timing, dose, and sequencing. The present application is directed to targets to mitigate immunologically acquired radioresistance.

Adenosine Signaling Modulators

The present application provides methods for use of compounds that modulate the expression level or activity of A2AR, A2BR, or a combination thereof, in a subject. The present application also provides methods for use of compounds that modulate the expression level or activity of CD73 in a subject. In addition, the present application provides methods for using such compounds for the treatment of cancer.

A2AR refers to adenosine A2a receptor. See GenBank ID 135 available at www.ncbi.nlm.nih.gov/gene/?term=135. The amino acid sequence of A2AR and nucleic acid sequences encoding A2AR are available in NCBI database. The consensus CDS sequences can be accessed using accession number CCDS13826.1 at www.ncbi.nlm.nih.gov/CCDS/CcdsBrowse.cgi.

A2BR refers to adenosine A2b receptor. See GenBank ID 136 available at www.ncbi.nlm.nih.gov/gene/?term=136. The amino acid sequence of A2BR and nucleic acid sequences encoding A2BR are available in NCBI database. The consensus CDS sequences can be accessed using accession number CCDS11173.1 at www.ncbi.nlm.nih.gov/CCDS/CcdsBrowse.cgi.

CD73 refers to 5'-nucleotidase ecto. See GenBank ID 4907 available at www.ncbi.nlm.nih.gov/gene/?term=4907. The amino acid sequence of CD73 and nucleic acid sequences encoding CD73 are available in NCBI database. The consensus CDS sequences for isoform 2 preproprotein can be accessed using accession number CCDS56439.1 and isoform 1 preproprotein can be accessed using accession number CCDS5002.1 at www.ncbi.nlm.nih.gov/CCDS/CcdsBrowse.cgi.

Adenosine signaling modulator refers to a compound that interacts with A2AR, A2BR, or both A2AR and A2BR and modulates its activity and/or its expression. For example, the compound can decrease the activity or expression of A2AR, A2BR, or both A2AR and A2BR. The compound can be an antagonist of A2AR, A2BR, or both A2AR and A2BR (e.g., an A2AR, A2BR, or both A2AR and A2BR inhibitor). Some non-limiting examples of include peptides (such as peptide fragments, or antibodies or fragments thereof), small molecules, and nucleic acids (such as siRNA or antisense RNA specific for a nucleic acid encoding A2AR, A2BR, or both A2AR and A2BR). Antagonists decrease the amount or the duration of the activity of A2AR, A2BR, or both A2AR and A2BR. Antagonists include proteins, nucleic acids, antibodies, small molecules, or any other molecule which decrease the activity of A2AR, A2BR, or both A2AR and A2BR.

Adenosine signaling modulator also refers to a compound that interacts with CD73 and modulates its activity and/or its expression. For example, the compound can decrease the activity or expression of CD73. The compound can be an antagonist of CD73 (e.g., a CD73 inhibitor). Some non-limiting examples of include peptides (such as peptide fragments, or antibodies or fragments thereof), small molecules, and nucleic acids (such as siRNA or antisense RNA specific for a nucleic acid encoding CD73). Antagonists decrease the amount or the duration of the activity of CD73. Antagonists include proteins, nucleic acids, antibodies, small molecules, or any other molecule which decrease the activity of CD73.

In various embodiments, adenosine signaling is modulated by use of antagonists of A2AR and A2BR and antagonists of CD73.

An adenosine signaling modulator can be a protein, such as an antibody (monoclonal, polyclonal, humanized, chimeric, or fully human), or a binding fragment thereof, directed against A2AR, A2BR, or both A2AR and A2BR, or against CD73. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab') 2, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) *Ann. Rev. Biomed. Eng.* 2:339-76; Hudson (1998) *Curr. Opin. Biotechnol.* 9:395-402). Antibodies can be obtained commercially, custom generated, or synthesized against an antigen of interest according to methods established in the art (see U.S. Pat. Nos. 6,914,128, 5,780,597, and 5,811,523; Roland E. Kontermann and Stefan Dübel (editors), Antibody Engineering, Vol. I & II, (2010) 2nd ed., Springer; Antony S. Dimitrov (editor), Therapeutic Antibodies: Methods and Protocols (Methods in Molecular Biology), (2009), Humana Press; Benny Lo (editor) Antibody Engineering: Methods and Protocols (Methods in Molecular Biology), (2004) Humana Press, each of which are hereby incorporated by reference in their entireties).

Inhibition of RNA encoding A2AR, A2BR, or both A2AR and A2BR, or encoding CD73 can effectively modulate the expression of these proteins and thus adenosine signalling. Inhibitors are selected from the group comprising: siRNA; interfering RNA or RNAi; dsRNA; RNA Polymerase III transcribed DNAs; ribozymes; and antisense nucleic acids, which can be RNA, DNA, or an artificial nucleic acid.

An adenosine signaling modulator can be a small molecule that binds to A2AR, A2BR, or both A2AR and A2BR, or to CD73 described herein and disrupts its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules can be identified via in silico screening or high-through-put (HTP) screening of combinatorial libraries according to methods established in the art (e.g., see Potyrailo et al., (2011) *ACS Comb Sci.* 13 (6): 579-633; Mensch et al., (2009) *J Pharm Sci.* 98 (12): 4429-68; Schnur (2008) *Curr Opin Drug Discov Devel.* 11 (3): 375-80; and Jhoti (2007) *Ernst Schering Found Symp Proc.* (3): 169-85, each of which are hereby incorporated by reference in their entireties.) Most conventional pharmaceuticals, such as aspirin, penicillin, and many chemotherapeutics, are small molecules, can be obtained commercially, can be chemically synthesized, or can be obtained from random or combinatorial libraries as described below (see, e.g., Werner et al., (2006) *Brief Funct. Genomic Proteomic* 5 (1): 32-6).

One non-limiting example of A2AR and A2BR antagonist is compound AB928 also known as etrumadenant. Structures of A2AR and A2BR antagonist useful for the present application include, but are not limited to: compound AB928 also known as etrumadenant (see pubchem.ncbi.nlm.nih.gov/compound/ab928):

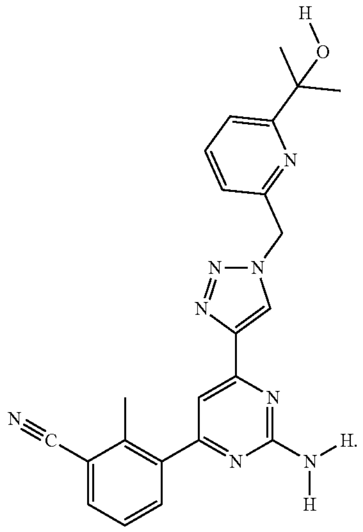

One non-limiting example of CD73 antagonist is compound AB680 also known as quemliclustat. Structures of CD73 antagonist useful for the present application include, but are not limited to: compound AB680 also known as quemliclustat (see pubchem.ncbi.nlm.nih.gov/compound/Quemliclustat):

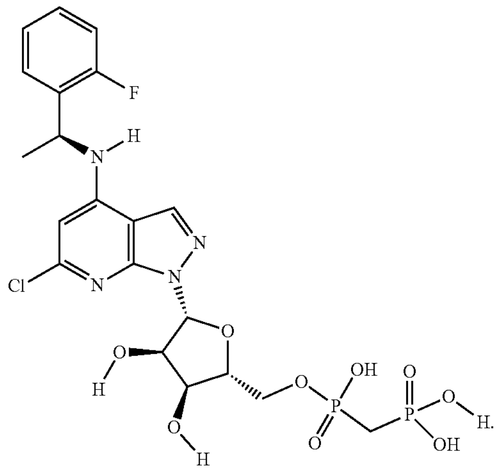

Pharmaceutical Compositions, Methods of Administration and Combination Treatments In some embodiments, adenosine signaling modulators and/or immune-based therapies can be supplied in the form of a pharmaceutical composition, comprising an isotonic excipient prepared under sufficiently sterile conditions for human administration. Choice of the excipient and any accompanying elements of the composition will be adapted in accordance with the route and device used for administration. In some embodiments, a composition comprising an adenosine signaling modulators or an immune-based therapy can also comprise, or be accompanied with, one or more other ingredients that facilitate the delivery or functional mobilization of the treatment.

These methods described herein are by no means all-inclusive, and further methods to suit the specific application is understood by the ordinary skilled artisan. Moreover, the effective amount of the compositions can be further approximated through analogy to compounds known to exert the desired effect.

According to the present application, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Pharmaceutical compositions for use in accordance with the present application can be formulated in conventional manner using one or more physiologically acceptable carriers or excipients. The therapeutic compositions of the present application can be formulated for a variety of routes of administration, including systemic and topical or localized administration. Techniques and formulations generally can be found in Remington's Pharmaceutical Sciences, Meade Publishing Co., Easton, Pa ($20^{th}$ ed., 2000), the entire disclosure of which is herein incorporated by reference. For systemic administration, an injection is useful, including intramuscular, intravenous, intraperitoneal, and subcutaneous. For injection, the therapeutic compositions of the present application can be formulated in liquid solutions, for example in physiologically compatible buffers, such as PBS, Hank's solution, or Ringer's solution. In addition, the therapeutic compositions can be formulated in solid form and redissolved or suspended immediately prior to use. Lyophilized forms are also included. Pharmaceutical compositions of the present application are characterized as being at least sterile and pyrogen-free. These pharmaceutical formulations include formulations for human and veterinary use.

Any of the therapeutic applications described herein can be applied to any subject in need of such therapy, including, for example, a mammal such as a dog, a cat, a cow, a horse, a rabbit, a monkey, a pig, a sheep, a goat, or a human. In some embodiments, the subject is a human.

A pharmaceutical composition of the present application is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

The dosage administered can be a therapeutically effective amount of the composition sufficient to result in treatment of a cancer, a decrease in cell proliferation, or a decrease in tumor growth, and can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

Toxicity and therapeutic efficacy of therapeutic compositions of the present application can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutic agents that exhibit large therapeutic indices are useful. Therapeutic compositions that exhibit some toxic side effects can be used.

Experimental animals can be used as models for human disease. For example, mice can be used as a mammalian model system. The physiological systems that mammals possess can be found in mice, and in humans, for example. Certain diseases can be induced in mice by manipulating their environment, genome, or a combination of both.

Administration of adenosine signaling modulators and/or immune-based therapies is not restricted to a single route, but may encompass administration by multiple routes. Multiple administrations may be sequential or concurrent. Other modes of application by multiple routes will be apparent to one of skill in the art.

REFERENCES

Michael A. Postow, et al., *Immunologic Correlates of the Abscopal Effect in a Patient with Melanoma*, New Eng. J. Med. (2012) 366, 925-931.

Yazan Abuodeh, et al., *Systematic Review of Case Reports on the Abscopal Effect*, Current Problems in Cancer (2016) 40, 25-37.

S. J. Antonia, et al., *Durvalumab After Chemoradiotherapy in Stage III Non-Small—Cell Lung Cancer*, New Eng. J. Med. (2017) 77, 1919-1929.

What is claimed is:

1. A method for treating cancer in a subject in need thereof, comprising administering to the subject one or more adenosine signaling modulators in combination with a radiation therapy, wherein the cancer is metastatic.

2. The method of claim 1, wherein the method further comprises administering to the subject an immune-based therapy.

3. The method of claim 2, wherein the immune-based therapy comprises administering the subject a therapeutic agent that activates the immune system of the subject.

4. The method of claim 2, wherein the immune-based therapy comprises administering the subject a therapeutic agent that suppresses the immune system of the subject.

5. The method of claim 2, wherein the immune-base therapy comprises administering the subject a therapeutic agent that regulates programmed cell death protein 1 (PD-1), programmed Cell Death Ligand 1 (PD-L1), or a combination thereof.

6. The method of claim 5, wherein the therapeutic agent is selected from the group consisting of pembrolizumab, nivolumab, cemiplimab, dostarlimab, atezolizumab, ipilimumab, avelumab, durvalumab, zimberelimab and combinations thereof.

7. The method of claim 1, wherein the adenosine signaling modulator is an A2AR and A2BR antagonist or a CD73 antagonist.

8. The method of claim 7, wherein the adenosine signaling modulator is etrumadenant having the structure:

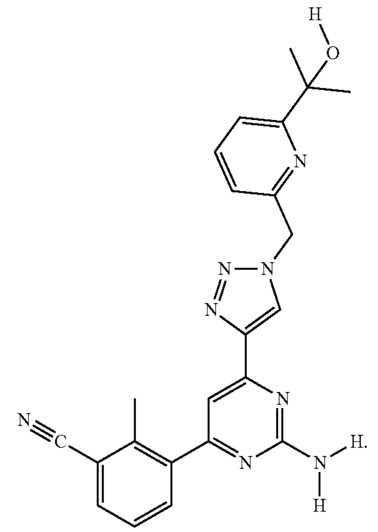

9. The method of claim 7, wherein the adenosine signaling modulator is quemliclustat having the structure:

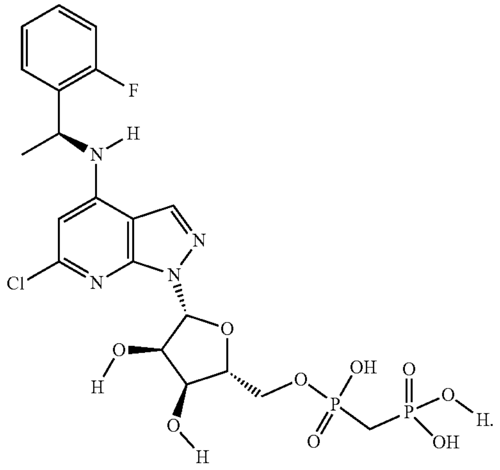

10. The method of claim 1, wherein the cancer comprises a solid tumor.

11. The method of claim 1, wherein the cancer is breast cancer, pancreatic cancer, prostate cancer, melanoma, basal cell cancer, colorectal cancer, bladder cancer, kidney cancer, thyroid cancer, uterine cancer, lung cancer, or a combination thereof.

12. The method of claim 1, wherein the subject is a human.

13. The method of claim 1, wherein the radiation therapy is administered for 1 day, 2 days, 3 days, 4 days, 5 days, 6 days, or 7 days.

14. The method of claim 1, wherein the radiation therapy is administered at a dose of about 8 gray.

15. A method for treating cancer in a subject in need thereof, comprising administering to the subject one or more adenosine signaling modulators in combination with a radiation therapy, wherein the radiation therapy is administered at a dose of about 8 gray.

16. The method of claim 15, wherein the method further comprises administering to the subject an immune-based therapy.

17. The method of claim 15, wherein the adenosine signaling modulator is an A2AR and A2BR antagonist or a CD73 antagonist.

18. The method of claim 17, wherein the adenosine signaling modulator is etrumadenant having the structure:

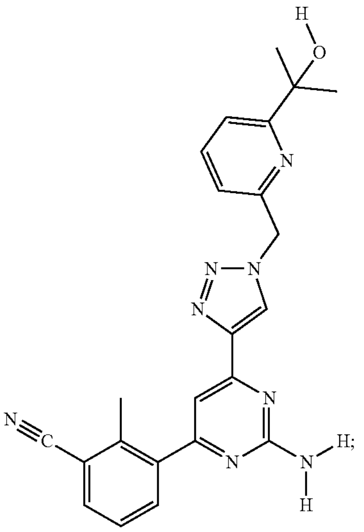

or quemliclustat having the structure:

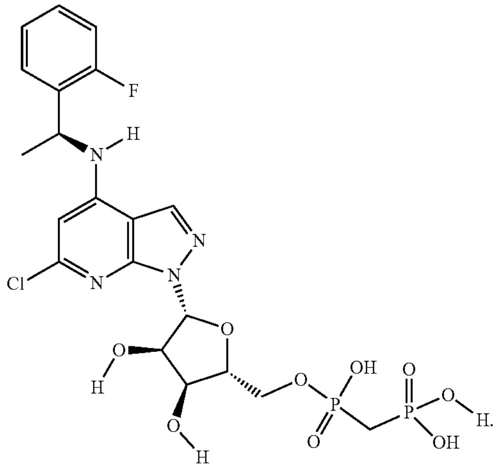

19. The method of claim 15, wherein the cancer is metastatic.

20. The method of claim 16, wherein the immune-based therapy comprises administering the subject a therapeutic agent that regulates programmed cell death protein 1 (PD-1), programmed Cell Death Ligand 1 (PD-L1), or a combination thereof.

* * * * *